US012582470B2

(12) United States Patent
Hagstrom et al.

(10) Patent No.: US 12,582,470 B2
(45) Date of Patent: Mar. 24, 2026

(54) ARCHITECTURES FOR HIGH DENSITY MAPPING AND ABLATING CATHETERS USING FLEXIBLE CIRCUIT BOARDS

(71) Applicant: Boston Scientific Scimed, Inc., Maple Grove, MN (US)

(72) Inventors: Nathan P. Hagstrom, Minneapolis, MN (US); Brian Soltis, St. Paul, MN (US); Edward J. Maierhofer, Brooklyn Park, MN (US); Andrew L. DeKock, Ham Lake, MN (US); Brendan E. Koop, Ham Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 317 days.

(21) Appl. No.: 18/510,178

(22) Filed: Nov. 15, 2023

(65) Prior Publication Data

US 2024/0197394 A1 Jun. 20, 2024

Related U.S. Application Data

(60) Provisional application No. 63/387,377, filed on Dec. 14, 2022.

(51) Int. Cl.
A61B 18/14 (2006.01)
*A61B 18/00* (2006.01)

(52) U.S. Cl.
CPC ..................... *A61B 18/1492* (2013.01); *A61B 2018/00351* (2013.01); *A61B 2018/00577* (2013.01);
(Continued)

(58) Field of Classification Search
CPC ...... A61B 18/1492; A61B 2018/00267; A61B 2018/00351; A61B 2018/00577;
(Continued)

(56) References Cited

U.S. PATENT DOCUMENTS 5,991,650 A 11/1999 Swanson et al.
9,655,677 B2 * 5/2017 Salahieh ................ A61B 5/287
(Continued)

FOREIGN PATENT DOCUMENTS

EP 3451962 B1 3/2020
EP 3991681 A1 5/2022
WO 2022032183 A1 2/2022

OTHER PUBLICATIONS

International Search Report and Written Opinion, PCT/US203/079872, Feb. 26, 2024, pp. 1-197.

*Primary Examiner* — Michael F Peffley
(74) *Attorney, Agent, or Firm* — Nelson Mullins Riley & Scarborough LLP

(57) ABSTRACT

A catheter for ablation of tissue through irreversible electroporation includes an electrode assembly comprising a flexible circuit having a distally located central flex circuit hub and a plurality of flex circuit branches extending proximally from the hub portion, each of the flex circuit branches defining, at least in part, an electrode assembly spline. The flexible circuit further includes a distal ablation electrode including an ablation electrode hub portion, and a plurality of radial segments integrally formed with the ablation electrode hub portion, each of the radial segments extending proximally along a portion of a respective one of the flex circuit branches and terminating in a proximal end, a plurality of proximal ablation electrodes, each of the proximal ablation electrodes located on a respective one of the flex circuit branches and having a distal end spaced from the proximal end of the adjacent radial segment of the distal ablation electrode.

20 Claims, 13 Drawing Sheets

(52) U.S. Cl.
CPC .............. *A61B 2018/00613* (2013.01); *A61B*
*2018/00875* (2013.01); *A61B 2018/1417*
(2013.01)

(58) Field of Classification Search
CPC ........... A61B 2018/00613; A61B 2018/00875;
A61B 2018/1417; A61B 2018/1467
See application file for complete search history.

(56) References Cited

U.S. PATENT DOCUMENTS

| | | | |
|---|---|---|---|
| 10,918,306 B2 * | 2/2021 | Govari ................ | A61B 5/6859 |
| 2017/0312007 A1 * | 11/2017 | Harlev .............. | A61B 18/1482 |
| 2018/0168511 A1 * | 6/2018 | Hall .................. | A61M 25/0074 |
| 2019/0216347 A1 * | 7/2019 | Ghodrati ............. | A61B 5/6858 |

* cited by examiner

ARCHITECTURES FOR HIGH DENSITY MAPPING AND ABLATING CATHETERS USING FLEXIBLE CIRCUIT BOARDS

CROSS-REFERENCE TO RELATED APPLICATIONS

This application claims the benefit of U.S. Provisional Application No. 63/387,377, entitled "ARCHITECTURES FOR HIGH DENSITY MAPPING AND ABLATING CATHETERS USING FLEXIBLE CIRCUIT BOARDS," and filed Dec. 14, 2022, which is hereby incorporated by reference in its entirety.

TECHNICAL FIELD

The present disclosure relates to medical systems and methods for ablating tissue in a patient. More specifically, the present disclosure relates to medical systems and methods for ablation of tissue by electroporation.

BACKGROUND

Ablation procedures are used to treat many different conditions in patients. Ablation can be used to treat cardiac arrhythmias, benign tumors, cancerous tumors, and to control bleeding during surgery. Usually, ablation is accomplished through thermal ablation techniques including radiofrequency (RF) ablation and cryoablation. In RF ablation, a probe is inserted into the patient and radio frequency waves are transmitted through the probe to the surrounding tissue. The radio frequency waves generate heat, which destroys surrounding tissue and cauterizes blood vessels. In cryoablation, a hollow needle or cryoprobe is inserted into the patient and cold, thermally conductive fluid is circulated through the probe to freeze and kill the surrounding tissue. RF ablation and cryoablation techniques indiscriminately kill tissue through cell necrosis, which may damage or kill otherwise healthy tissue, such as tissue in the esophagus, phrenic nerve cells, and tissue in the coronary arteries.

Another ablation technique uses electroporation. In electroporation, or electro-permeabilization, an electrical field is applied to cells to increase the permeability of the cell membrane. The electroporation can be reversible or irreversible, depending on the strength of the electric field. If the electroporation is reversible, the increased permeability of the cell membrane can be used to introduce chemicals, drugs, and/or deoxyribonucleic acid (DNA) into the cell, prior to the cell healing and recovering. If the electroporation is irreversible, the affected cells are killed through apoptosis.

Irreversible electroporation can be used as a nonthermal ablation technique. In irreversible electroporation, trains of short, high voltage pulses are used to generate electric fields that are strong enough to kill cells through apoptosis. In ablation of cardiac tissue, irreversible electroporation can be a safe and effective alternative to the indiscriminate killing of thermal ablation techniques, such as RF ablation and cryoablation. Irreversible electroporation can be used to kill targeted tissue, such as myocardium tissue, by using an electric field strength and duration that kills the targeted tissue but does not permanently damage other cells or tissue, such as non-targeted myocardium tissue, red blood cells, vascular smooth muscle tissue, endothelium tissue, and nerve cells. There is a continuing need for improved devices and methods for performing cardiac tissue ablation through irreversible electroporation.

SUMMARY

In Example 1, a catheter for ablating cardiac tissue through irreversible electroporation, the catheter comprising a tubular outer shaft having a proximal end and an opposite distal end, and an electrode assembly extending distally from the distal end of the outer shaft. The electrode assembly defines a distally located central hub portion and a plurality of splines each including a distal end portion extending from the central hub portion, and a proximal end portion attached to and constrained by the outer shaft, the electrode assembly comprising a flexible circuit having a flex circuit hub and a plurality of flex circuit branches extending proximally from the flex circuit hub. The flexible circuit further includes a distal ablation electrode including an ablation electrode hub portion located on the flex circuit hub, and a plurality of radial segments integrally formed with the ablation electrode hub portion, each of the radial segments extending proximally along a portion of a respective one of the flex circuit branches and terminating in a proximal end, and a plurality of proximal ablation electrodes, each of the proximal ablation electrodes located on a respective one of the flex circuit branches and having a distal end spaced from the proximal end of the adjacent radial segment of the distal ablation electrode.

In Example 2, the catheter of Example 1, further comprising a plurality of spline sensing electrodes located on each spline.

In Example 3, the catheter of Example 2, wherein a distal-most spline sensing electrode on each spline is disposed within a periphery of each of the radial segments of the distal ablation electrode and is electrically isolated from the distal ablation electrode.

In Example 4, the catheter of either of Examples 2 or 3, wherein one or more of the plurality of spline sensing electrodes is disposed within a periphery of each of the proximal ablation electrodes and is electrically isolated therefrom.

In Example 5, the catheter of any of Examples 1-4, wherein the proximal end of each radial segment has a semi-circular shape.

In Example 6, the catheter of any of Examples 1-5, wherein the distal end of each proximal ablation electrode has a semi-circular shape.

In Example 7, the catheter of any of Examples 1-6, wherein each of the proximal ablation electrodes includes one or more proximal ablation electrode apertures formed therein, and wherein one of the spline sensing electrodes is disposed within a respective one of the proximal ablation electrode apertures.

In Example 8, the catheter of Example 7, wherein each proximal ablation electrode aperture is bounded by respective inner peripheral surface of the proximal ablation electrode, and wherein an outer peripheral surface of each spline sensing electrode is spaced from the respective inner peripheral surface of the proximal ablation electrode.

In Example 9, the catheter of any of Examples 3-8, wherein each of the radial segments of the distal ablation electrode includes a proximal portion having a radial segment aperture formed therein, and wherein each of the distal-most spline sensing electrodes is disposed within a respective one of the radial segment apertures.

In Example 10, the catheter of Example 9, wherein each radial segment aperture is bounded by respective inner peripheral surface of the radial segment, and wherein an outer peripheral surface of each distal-most spline sensing electrode is spaced from the respective inner peripheral surface of the radial segment.

In Example 11, the catheter of either of Examples 9 or 10, wherein each of the radial segments has a distal portion opposite the proximal portion, the proximal portion having a greater lateral width than the distal portion.

In Example 12, the catheter of any of Examples 1-11, further comprising a hub sensing electrode centrally located on the central hub portion of the electrode assembly.

In Example 13, the catheter of any of Examples 1-12, wherein the splines each have lateral edges having an atraumatic shape.

In Example 14, the catheter of any of Examples 1-13, further comprising a central post extending distally from the distal end of the tubular shaft and into an inner space defined by the electrode assembly when the electrode assembly is in an expanded configuration, the central post including a reference electrode.

In Example 15, the catheter of any of Examples 1-14, wherein the electrode assembly further comprises a support member having a support member hub and a plurality of support member branches extending proximally from the support member hub, wherein the flex circuit hub is disposed over the support member hub, and each of the flex circuit branches is disposed over a respective one of the support member branches.

Example 16 is a catheter for ablating cardiac tissue through irreversible electroporation, the catheter comprising a tubular outer shaft having a proximal end and an opposite distal end, and an electrode assembly extending distally from the distal end of the outer shaft, the electrode assembly defining a distally located central hub portion and a plurality of splines each including a distal end portion extending from the central hub portion, and a proximal end portion attached to and constrained by the outer shaft. The electrode assembly comprises a support member and a flexible circuit. The support member has a support member hub and a plurality of support member branches extending proximally from the support member hub. The flexible circuit is attached to an outer surface of the support member and has a flex circuit hub disposed over the support member hub, and a plurality of flex circuit branches, each of the flex circuit branches being disposed over a respective one of the support member branches. The flexible circuit further includes a distal ablation electrode, and a plurality of proximal ablation electrodes. The distal ablation electrode includes an ablation electrode hub portion located on the flex circuit hub, and a plurality of radial segments integrally formed with the ablation electrode hub portion, each of the radial segments extending proximally along a portion of a respective one of the flex circuit branches and terminating in a proximal end. Each of the proximal ablation electrodes is located on a respective one of the flex circuit branches and has a distal end spaced from the proximal end of the adjacent radial segment of the distal ablation electrode.

In Example 17, the catheter of Example 16, wherein the flexible circuit further comprises a plurality of spline sensing electrodes located on each spline, wherein a distal-most spline sensing electrode on each spline is disposed within a periphery of each of the radial segments of the distal ablation electrode and is electrically isolated from the distal ablation electrode, and wherein one or more of the plurality of spline sensing electrodes is disposed within a periphery of each of the proximal ablation electrodes and is electrically isolated therefrom.

In Example 18, the catheter of Example 17, wherein the proximal end of each radial segment has a semi-circular shape.

In Example 19, the catheter of Example 18, wherein the distal end of each proximal ablation electrode has a semi-circular shape.

In Example 20, the catheter of Example 17, wherein each of the proximal ablation electrodes includes one or more proximal ablation electrode apertures formed therein, and wherein one of the spline sensing electrodes is disposed within a respective one of the proximal ablation electrode apertures.

In Example 21, the catheter of Example 20, wherein each proximal ablation electrode aperture is bounded by respective inner peripheral surface of the proximal ablation electrode, and wherein an outer peripheral surface of each spline sensing electrode is spaced from the respective inner peripheral surface of the proximal ablation electrode.

In Example 22, the catheter of Example 17, wherein each of the radial segments of the distal ablation electrode includes a proximal portion having a radial segment aperture formed therein, and wherein each of the distal-most spline sensing electrodes is disposed within a respective one of the radial segment apertures.

In Example 23, the catheter of Example 22, wherein each radial segment aperture is bounded by respective inner peripheral surface of the radial segment, and wherein an outer peripheral surface of each distal-most spline sensing electrode is spaced from the respective inner peripheral surface of the radial segment.

In Example 24, the catheter of Example 17, further comprising a hub sensing electrode centrally located on the central hub portion of the electrode assembly.

In Example 25, the catheter of Example 17, further comprising a central post extending distally from the distal end of the tubular shaft and into an inner space defined by the electrode assembly when the electrode assembly is in an expanded configuration, the central post including a reference electrode.

Example 26 is a catheter for ablating cardiac tissue through irreversible electroporation, the catheter comprising a tubular outer shaft having a proximal end and an opposite distal end, and an electrode assembly extending distally from the distal end of the outer shaft, the electrode assembly defining a distally-located central hub portion and a plurality of splines each including a distal end portion extending proximally from the central hub portion, and a proximal end portion attached to and constrained by the outer shaft. The electrode assembly comprises a support member and a flexible circuit. The support member is formed from a superelastic material and has a support member hub and a plurality of support member branches integrally formed with and extending proximally from the support member hub. The flexible circuit is attached to an outer surface of the support member and has a flex circuit hub disposed over the support member hub, and a plurality of flex circuit branches integrally formed with the flex circuit hub, each of the flex circuit branches being disposed over a respective one of the support member branches. The flexible circuit further includes a distal ablation electrode, a plurality of proximal ablation electrodes, and a plurality of spline sensing electrodes. The distal ablation electrode includes an ablation electrode hub portion located on the flex circuit hub, and a plurality of radial segments integrally formed with the ablation electrode hub portion, each of the radial segments extending proximally along a portion of a respective one of the flex circuit branches. Each of the proximal ablation electrodes is located on a respective one of the flex circuit branches. The plurality of spline sensing electrodes includes a plurality of distal spline sensing electrodes each being disposed within a periphery of a respective one of the radial segments of the distal ablation electrode and electrically isolated from the distal ablation electrode, and one or more proximal spline sensing electrodes disposed within a periphery of each of the proximal ablation electrodes and electrically isolated therefrom.

In Example 27, the catheter of Example 26, wherein each of the proximal ablation electrodes has a proximal end and a distal end having a semi-circular shape, and wherein each of the radial segments has a proximal end having a semi-circular shape.

In Example 28, the catheter of Example 26, wherein each of the proximal ablation electrodes includes one or more proximal ablation electrode apertures formed therein, and wherein each of the proximal spline sensing electrodes is disposed within a respective one of the proximal ablation electrode apertures.

In Example 29, the catheter of Example 28, wherein each proximal ablation electrode aperture is bounded by respective inner peripheral surface of the proximal ablation electrode, and wherein an outer peripheral surface of each proximal spline sensing electrode is spaced from the respective inner peripheral surface of the proximal ablation electrode.

In Example 30, the catheter of Example 26, wherein each of the radial segments of the distal ablation electrode includes proximal portion having a radial segment aperture formed therein, and wherein each of the distal spline sensing electrodes is disposed within a respective one of the radial segment apertures.

In Example 31, the catheter of Example 30, wherein each radial segment aperture is bounded by respective inner peripheral surface of the radial segment, and wherein an outer peripheral surface of each distal spline sensing electrode is spaced from the respective inner peripheral surface of the radial segment.

Example 32 is a catheter for ablating cardiac tissue through irreversible electroporation, the catheter comprising a tubular outer shaft having a proximal end and an opposite distal end, and an electrode assembly extending distally from the distal end of the outer shaft. The electrode assembly comprises a flexible circuit having a distally located central flex circuit hub and a plurality of flex circuit branches extending proximally from the hub portion, each of the flex circuit branches defining, at least in part, an electrode assembly spline and including a proximal end portion attached to and constrained by the outer shaft. The flexible circuit further includes a distal ablation electrode and a plurality of proximal ablation electrodes. The distal ablation electrode includes an ablation electrode hub portion located on the flex circuit hub, and a plurality of radial segments integrally formed with the ablation electrode hub portion, each of the radial segments extending proximally along a portion of a respective one of the flex circuit branches and terminating in a proximal end. Each of the proximal ablation electrodes is located on a respective one of the flex circuit branches and has a distal end spaced from the proximal end of the adjacent radial segment of the distal ablation electrode.

In Example 33, the catheter of Example 32, wherein the proximal end of each radial segment has a semi-circular shape, and wherein the distal end of each proximal ablation electrode has a semi-circular shape.

In Example 34, the catheter of Example 33, wherein the flexible circuit further comprises a plurality of spline sensing electrodes located on each spline, wherein a distal-most spline sensing electrode on each spline is disposed within a periphery of each of the radial segments of the distal ablation electrode and is electrically isolated from the distal ablation electrode, and wherein one or more of the plurality of spline sensing electrodes is disposed within a periphery of each of the proximal ablation electrodes and electrically isolated therefrom.

In Example 35, the catheter of Example 34, wherein the flexible circuit further comprises a hub sensing electrode centrally located on the flex circuit hub.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
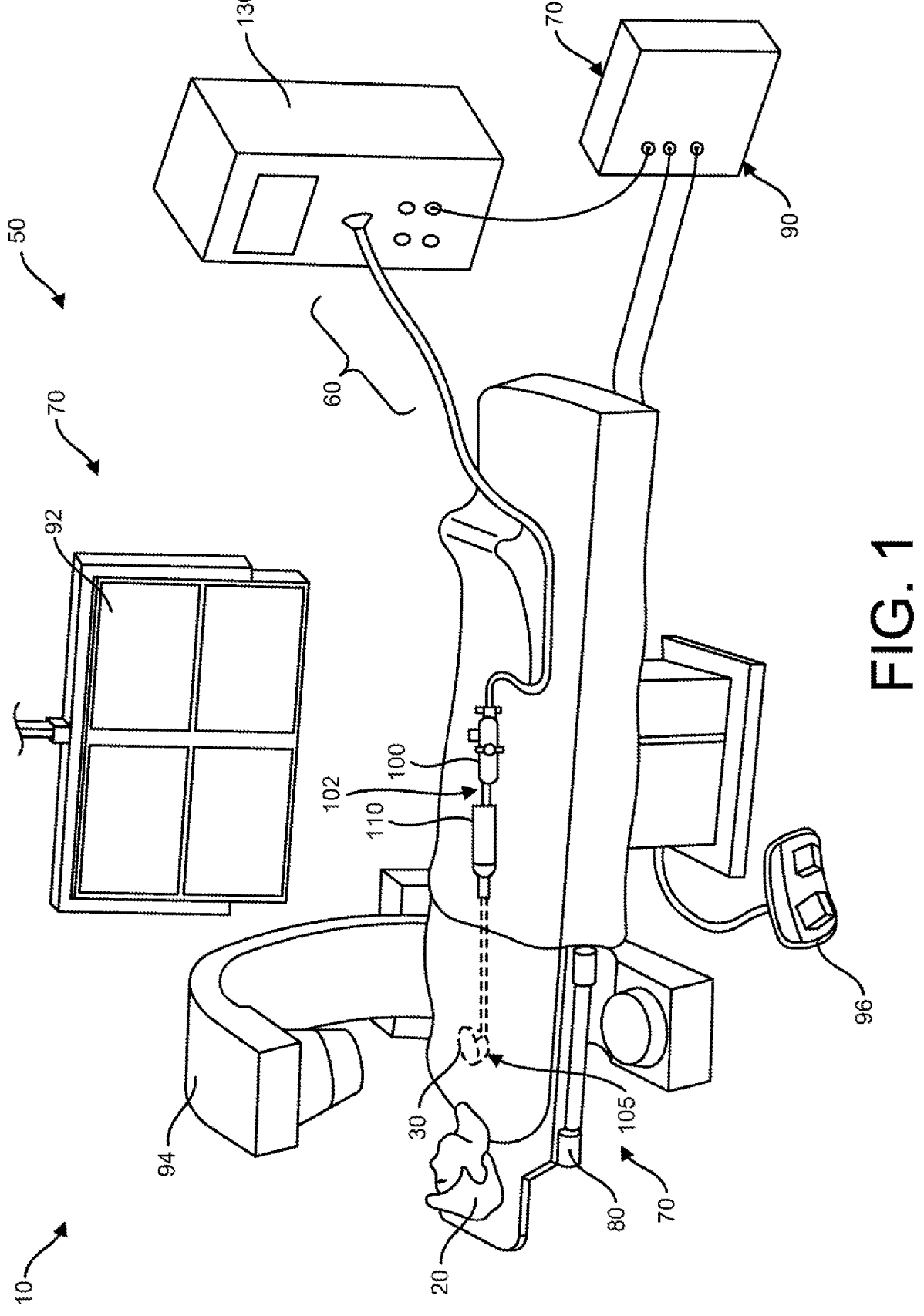
FIG. 1 is a diagram illustrating an exemplary clinical setting for treating a patient, and for treating a heart of the patient, using an electrophysiology system, in accordance with embodiments of the subject matter of the disclosure.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

For purposes of promoting an understanding of the principles of the present disclosure, reference is now made to the examples illustrated in the drawings, which are described below. The illustrated examples disclosed herein are not intended to be exhaustive or to limit the disclosure to the precise form disclosed in the following detailed description. Rather, these exemplary embodiments were chosen and described so that others skilled in the art may use their teachings. It is not beyond the scope of this disclosure to have a number (e.g., all) the features in a given example used across all examples. Thus, no one figure should be interpreted as having any dependency or requirement related to any single component or combination of components illustrated therein. Additionally, various components depicted in a given figure may be, in examples, integrated with various ones of the other components depicted therein (and/or components not illustrated), all of which are considered to be within the ambit of the present disclosure.

The terms "couples," "coupled," "connected," "attached," and the like along with variations thereof are used to include both arrangements wherein two or more components are in direct physical contact and arrangements wherein the two or more components are not in direct contact with each other (e.g., the components are "coupled" via at least a third component), but yet still cooperate or interact with each other.

Throughout the present disclosure and in the claims, numeric terminology, such as first and second, is used in reference to various components or features. Such use is not intended to denote an ordering of the components or features. Rather, numeric terminology is used to assist the reader in identifying the component or features being referenced and should not be narrowly interpreted as providing a specific order of components or features.

FIG. 1 is a diagram illustrating an exemplary clinical setting 10 for treating a patient 20, and for treating a heart 30 of the patient 20, using an electrophysiology system 50, in accordance with embodiments of the subject matter of the disclosure. The electrophysiology system 50 includes an electroporation catheter system 60 and an electro-anatomical mapping (EAM) system 70, which includes a localization field generator 80, a mapping and navigation controller 90, and a display 92. Also, the clinical setting 10 includes additional equipment such as imaging equipment 94 (represented by the C-arm) and various controller elements, such as a foot controller 96, configured to allow an operator to control various aspects of the electrophysiology system 50. As will be appreciated by the skilled artisan, the clinical setting 10 may have other components and arrangements of components that are not shown in FIG. 1.

The electroporation catheter system 60 includes an electroporation catheter 100 having a proximal portion 102 and a distal portion 105, an introducer sheath 110, and an electroporation console 130. Additionally, the electroporation catheter system 60 includes various connecting elements, e.g., cables, umbilicals, and the like, that operate to functionally connect the components of the electroporation catheter system 60 to one another and to the components of the EAM system 70. This arrangement of connecting elements is not of critical importance to the present disclosure, and the skilled artisan will recognize that the various components described herein can be interconnected in a variety of ways.

In embodiments, the introducer sheath 110 is operable to provide a delivery conduit through which the electroporation catheter 100, in particular all or part of the distal portion 105 thereof, can be deployed to the specific target sites within the patient's heart 30.

In embodiments, the electroporation catheter system 60 is configured to deliver electric field energy to targeted tissue in the patient's heart 30 to create tissue apoptosis, rendering the tissue incapable of conducting electrical signals.

The electroporation console 130 is configured to control functional aspects of the electroporation catheter system 60. In embodiments, the electroporation console 130 includes one or more controllers, microprocessors, and/or computers that execute code out of memory to control and/or perform the functional aspects of the electroporation catheter system 60. In embodiments, the memory can be part of the one or more controllers, microprocessors, and/or computers, and/or part of memory capacity accessible through a network, such as the world wide web. In embodiments, the electroporation console 130 includes pulse generator hardware, software and/or firmware configure to generate electrical pulses in predefined waveforms, which are transmitted to electrodes on the electroporation catheter 100 to generate electric fields sufficient to achieve the desired clinical effect, in particular ablation of target tissue through irreversible electroporation. In embodiments, the electroporation console 130 can deliver the pulsed waveforms to the electroporation catheter 100 in a monopolar or bipolar mode of operation, as will be described in further detail herein.

The EAM system 70 is operable to track the location of the various functional components of the electroporation catheter system 60, and to generate high-fidelity three-dimensional anatomical and electro-anatomical maps of the cardiac chambers of interest. In embodiments, the EAM system 70 can be the RHYTHMIA™ HDx mapping system marketed by Boston Scientific Corporation. Also, in embodiments, the mapping and navigation controller 90 of the EAM system 70 includes one or more controllers, microprocessors, and/or computers that execute code out of memory to control and/or perform functional aspects of the EAM system 70, where the memory, in embodiments, can be part of the one or more controllers, microprocessors, and/or computers, and/or part of memory capacity accessible through a network, such as the world wide web.

As will be appreciated by the skilled artisan, the depiction of the electrophysiology system 50 shown in FIG. 1 is intended to provide a general overview of the various components of the system 50 and is not in any way intended to imply that the disclosure is limited to any set of components or arrangement of the components. For example, the skilled artisan will readily recognize that additional hardware components, e.g., breakout boxes, workstations, and the like, can and likely will be included in the electrophysiology system 50.

The EAM system 70 generates a localization field, via the field generator 80, to define a localization volume about the heart 30, and one or more location sensors or sensing elements on the tracked device(s), e.g., the electroporation catheter 100, generate an output that can be processed by the mapping and navigation controller 90 to track the location of the sensor, and consequently, the corresponding device, within the localization volume. In the illustrated embodiment, the device tracking is accomplished using magnetic tracking techniques, whereby the field generator 80 is a magnetic field generator that generates a magnetic field defining the localization volume, and the location sensors on the tracked devices are magnetic field sensors.

In other embodiments, impedance tracking methodologies may be employed to track the locations of the various devices. In such embodiments, the localization field is an electric field generated, for example, by an external field generator arrangement, e.g., surface electrodes, by intra-body or intra-cardiac devices, e.g., an intracardiac catheter, or both. In these embodiments, the location sensing elements can constitute electrodes on the tracked devices that generate outputs received and processed by the mapping and navigation controller 90 to track the location of the various location sensing electrodes within the localization volume.

In embodiments, the EAM system 70 is equipped for both magnetic and impedance tracking capabilities. In such embodiments, impedance tracking accuracy can, in some instances be enhanced by first creating a map of the electric field induced by the electric field generator within the cardiac chamber of interest using a probe equipped with a magnetic location sensor, as is possible using the aforementioned RHYTHMIA HDx™ mapping system. One exemplary probe is the INTELLAMAP ORION™ mapping catheter marketed by Boston Scientific Corporation.

Regardless of the tracking methodology employed, the EAM system 70 utilizes the location information for the various tracked devices, along with cardiac electrical activity acquired by, for example, the electroporation catheter 100 or another catheter or probe equipped with sensing electrodes, to generate, and display via the display 92, detailed three-dimensional geometric anatomical maps or representations of the cardiac chambers as well as electroanatomical maps in which cardiac electrical activity of interest is superimposed on the geometric anatomical maps. Furthermore, the EAM system 70 can generate a graphical representation of the various tracked devices within the geometric anatomical map and/or the electro-anatomical map.

Embodiments of the present disclosure provide systems, devices, and methods for selective and rapid application of pulsed electric fields to ablate tissue by irreversible electroporation. Generally, the systems, devices, and methods described herein may be used to generate large electric field magnitudes at desired regions of interest and reduce peak electric field values elsewhere in order to reduce unnecessary tissue damage and electrical arcing. An irreversible electroporation system as described herein may include a signal generator and a processor configured to apply one or more voltage pulse waveforms to a selected set of electrodes of an ablation device to deliver energy to a region of interest (e.g., ablation energy for a set of tissue in a pulmonary vein ostium or antrum). The pulse waveforms disclosed herein may aid in therapeutic treatment of a variety of cardiac arrhythmias (e.g., atrial fibrillation). In order to deliver the pulse waveforms generated by the signal generator, one or more electrodes of the ablation device may have an insulated electrical lead configured for sustaining a voltage potential in the order of several hundred volts to several thousand volts. The electrodes may be independently addressable such that each electrode may be controlled (e.g., deliver energy) independently of any other electrode of the device. In this manner, the electrodes may deliver different energy waveforms with different timing synergistically for electroporation of tissue.

Pulse waveforms for electroporation energy delivery as disclosed herein may enhance the safety, efficiency and effectiveness of energy delivery to tissue by reducing the electric field threshold associated with irreversible electroporation, thus yielding more effective ablative lesions with a reduction in total energy delivered. In some embodiments, the voltage pulse waveforms disclosed herein may be hierarchical and have a nested structure. For example, the pulse waveform may include hierarchical groupings of pulses having associated timescales. In some embodiments, the methods, systems, and devices disclosed herein may comprise one or more of the methods, systems, and devices described in International Application Serial No. PCT/US2016/057664, filed on Oct. 19, 2016, and titled "SYSTEMS, APPARATUSES AND METHODS FOR DELIV- ERY OF ABLATIVE ENERGY TO TISSUE," the contents of which are hereby incorporated by reference in its entirety.

Figure 2A:
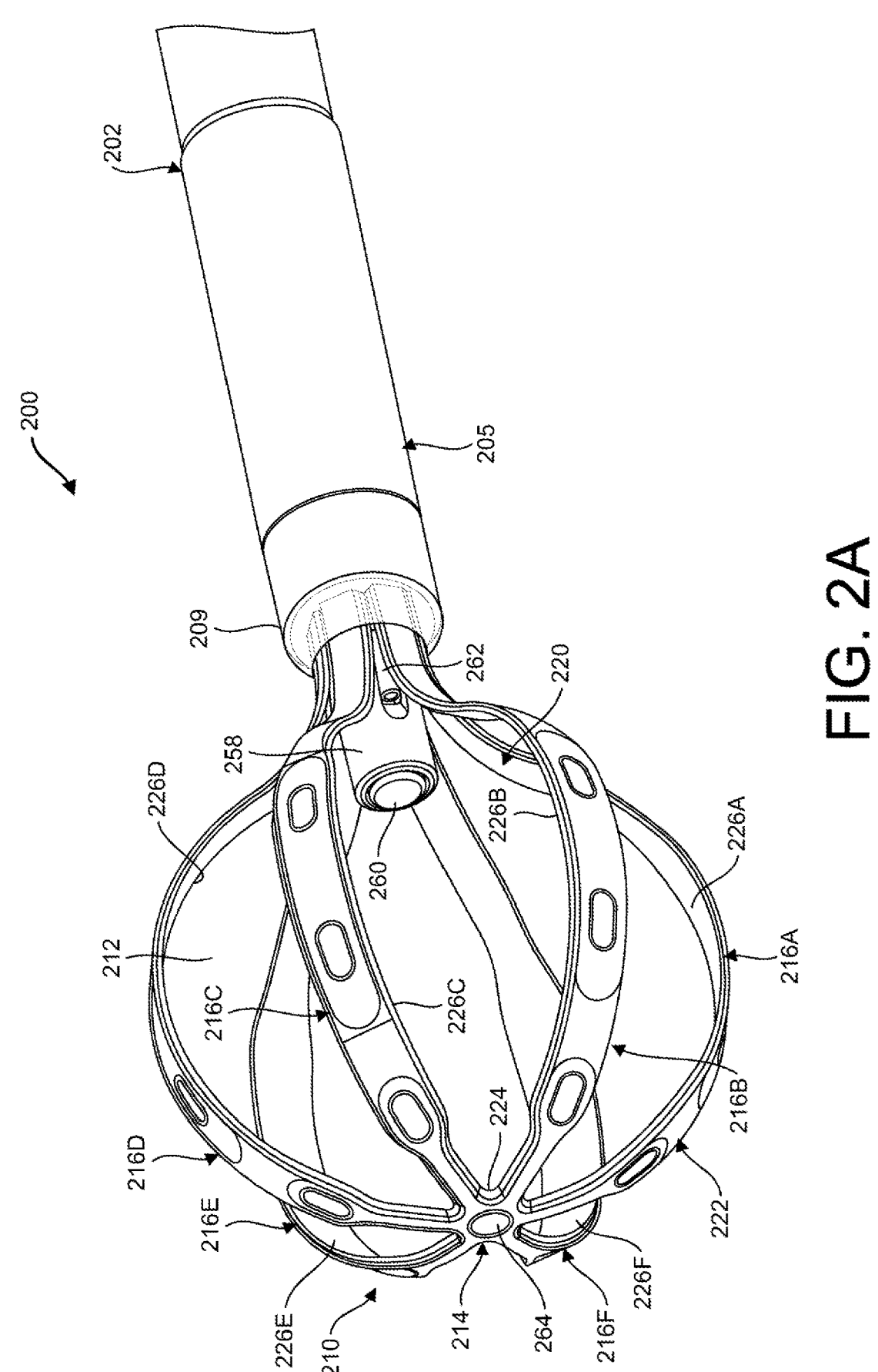
FIG. 2A is a perspective illustration of a distal portion of a splined catheter for use in the electrophysiology system of FIG. 1, in accordance with embodiments of the subject matter of the disclosure.

FIG. 2A partial perspective illustration of an electroporation catheter 200 having a catheter distal portion 205 according to an embodiment of the present disclosure. The electroporation catheter 200 corresponds to the electroporation catheter 100 described with respect to FIG. 1. The electroporation catheter 200 has a tubular outer shaft 208 having a shaft distal end 209, and an electrode assembly 210 extending distally from the distal end 209 of the outer shaft 208. In embodiments, the electrode assembly 210 is configured to self-expand from a collapsed configuration when constrained within a delivery sheath to a pre-defined expanded configuration defining an inner space 212. As will be explained in greater detail herein, the electrode assembly comprises multiple ablation electrodes configured to receive pulsed electrical signals/waveforms from the electroporation console 130 (FIG. 1), thereby creating pulsed electric fields sufficient for ablating target tissue via irreversible electroporation. Additionally, the electrode assembly 210 further includes a plurality of mapping and sensing electrodes configured for, among other things, sensing cardiac electrical signals, localization of the electrode assembly 210 within the patient anatomy (e.g., via the EAM system 70 of FIG. 1), and determining proximity to target tissue within the anatomy.

Overall, the electrode assembly 210 and other electrode assembly embodiments described herein within the scope of the present disclosure, is primarily designed for the creation of relatively localized ablation lesions (i.e., focal lesions), as compared to relatively large diameter circumferential lesions created in pulmonary vein isolation procedures). However, the skilled artisan will appreciate that the teachings of the present disclosure can be readily adapted for a catheter capable of large diameter circumferential lesions. The designs of the various electrode assembly embodiments described herein can provide the clinician with a wide range of capabilities for monopolar and bipolar focal pulsed field ablation of cardiac tissue, combined with the ability to perform localized (i.e., at the location of the delivery of pulsed field ablative energy), high fidelity sensing of cardiac tissue, e.g., for lesion or conduction block assessment, tissue contact determinations, and the like.

Figure 2B:
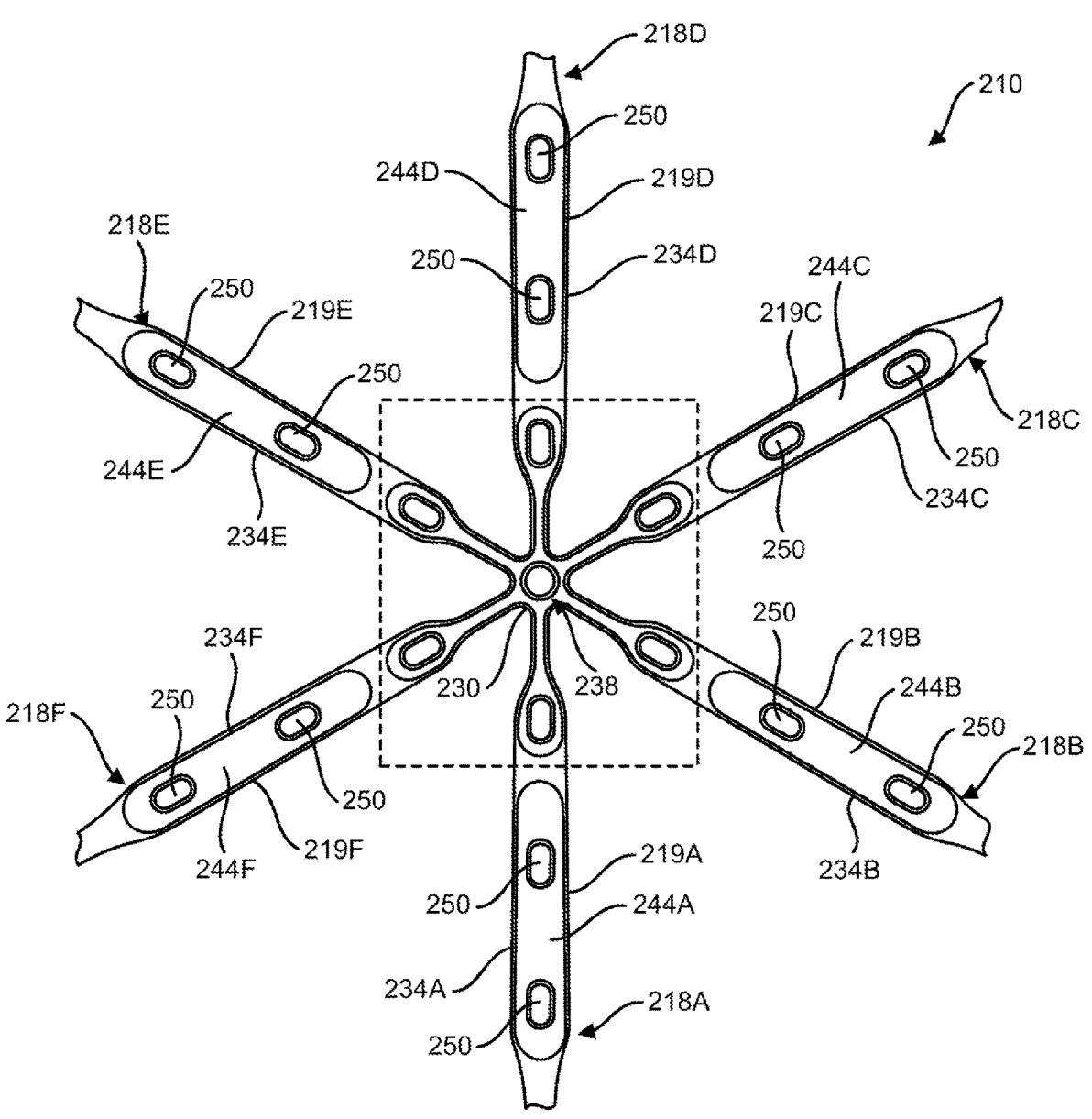
FIGS. 2B-2C are partial plan views an electrode assembly of the splined catheter shown in two-dimensions, in accordance with embodiments of the subject matter of the disclosure.
Figure 2C:
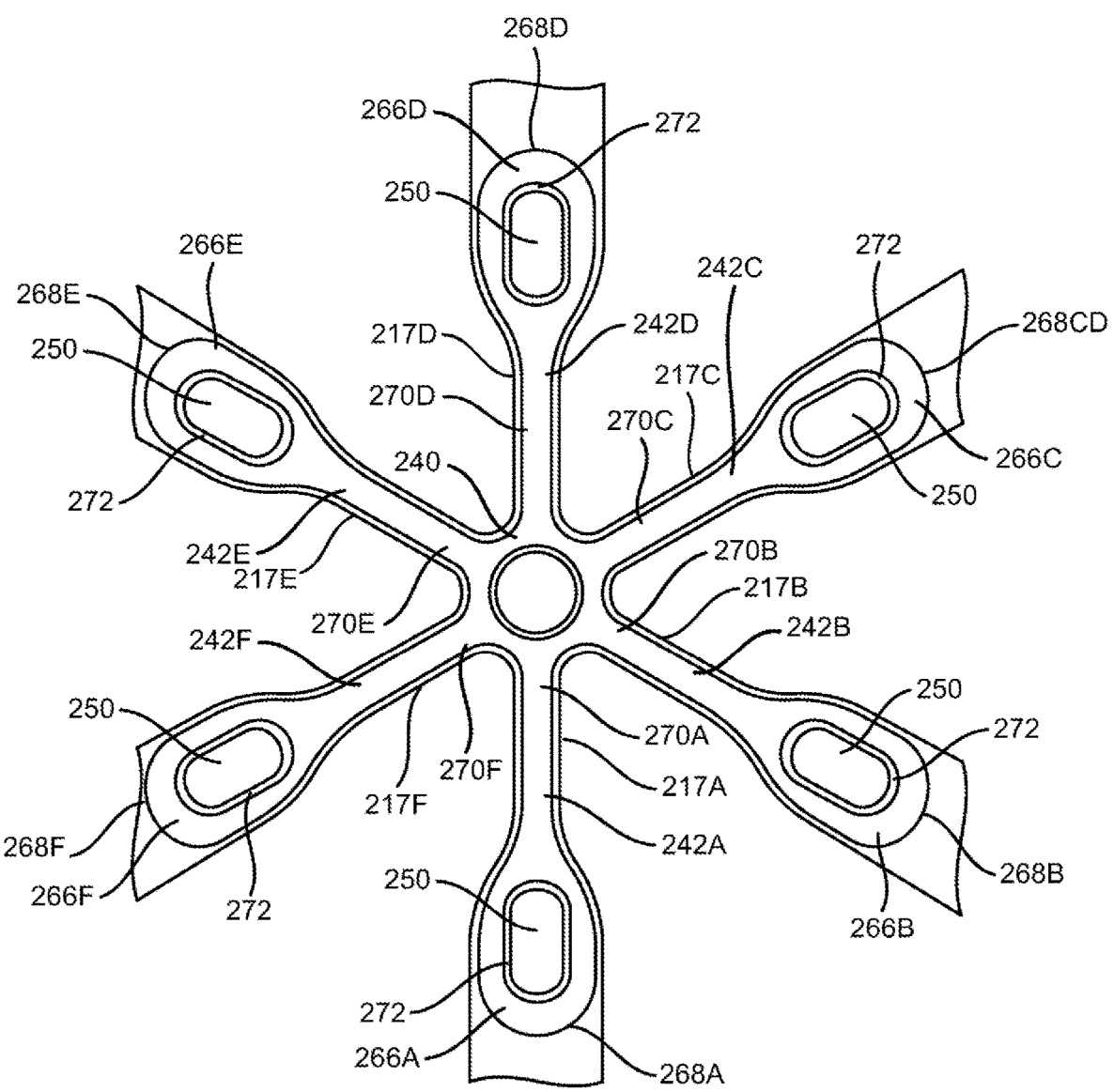

FIGS. 2B-2C are partial plan views the electrode assembly 210 of the electroporation catheter 200, shown in two-dimensions to illustrate the layout of the electrode assembly 210. Referring to FIGS. 2A-2C together, in the illustrated embodiment, the electrode assembly 210 as a whole has a distally-located central hub portion 214 and a plurality of splines 216A-216F extending proximally from the central hub portion 214. As further shown, each respective spline 216A-216F has a distal end portion 217A-217F, a proximal end portion 218A-218F, and an intermediate portion 219A-219F extending between the distal end portion 217A-217F and the proximal end portion 218A-218F. As shown, each of the proximal end portions 218A-218F is attached to and constrained by the distal end 209 of the outer shaft 202. As further shown, in the illustrated embodiment, the intermediate portion 219A-219F of each spline 216A-216F has a lateral width that is greater than the lateral width of each of the respective proximal end portion 218A-218F and the distal end portions 217A-217F. In embodiments, the particular geometry of the splines 216A-216F and the related components, e.g., ablation and mapping electrodes, is optimized to provide desired mechanical and therapeutic/diagnostic capabilities.

In the illustrated embodiment, the splines 216A-216F are composed of a support member 220 and a flexible circuit 222 secured to and disposed over an outer surface of the support member 222. The support member 220 functions, among other things, as a primary structural support of the electrode assembly 210, and thus primarily defines the mechanical characteristics of the electrode assembly 210. In embodiments, the support member 220 is formed from a superelastic material (metal or polymer) to provide desired mechanical/structural properties to the electrode assembly 210. In embodiments, the support member 220 is formed from a superelastic metal alloy, e.g., a nickel-titanium alloy.

The support member 220 includes a support member hub 224 and a plurality of support member branches 226A-226F. In embodiments, the support member branches 226A-226F are integrally formed with and extend proximally from the support member hub 224. For example, the entire support member 200 may be cut from a single sheet of material using conventional manufacturing techniques. This unitary structure provides robust structural properties, for example, selective flexibility and enhanced fatigue characteristics, particularly in areas that are subject to relatively high stresses during manufacture and use of the electroporation catheter 200. Forming the support member 220 from a superelastic material such as a nickel-titanium alloy facilitates configuring the support member 220 to assume its desired unconstrained shape such as shown in FIG. 2A due to the shape memory properties of the material, while providing sufficient flexibility necessary to collapse the electrode assembly 210 within a delivery sheath. In embodiments, the support member branches 226A-226F can be selectively configured along their lengths to tune the mechanical characteristics of the electrode assembly 210.

The flexible circuit 222 includes a flex circuit hub 230 and a plurality of flex circuit branches 234A-234F. In embodiments, the flex circuit hub 230 is disposed over and secured to the support member hub 224. In embodiments, the flex circuit branches 234A-234F are integrally formed with the flex circuit hub 230, and each of the flex circuit branches 234A-234F is disposed over and secured to a respective one of the support member branches 226A-226F. The flexible circuit 222 comprises a layered construction including one or more dielectric substrate layers, and conductive traces formed thereon. Similar to the support member 220, the unitary construction of the flexible circuit 222 enhances its structural properties, for example, by minimizing joints or other discontinuities at regions subject to relatively high stresses during use.

As shown, the flexible circuit 222 includes a distal ablation electrode 238 that has a distal ablation electrode hub portion 240 and a plurality of radial segments 242A-242F. In the illustrated embodiment, the distal ablation electrode hub portion 240 is located on the flex circuit hub 230. Additionally, the radial segments 242A-242F are integrally formed with the distal ablation electrode hub portion 240. Each of the radial segments 242A-242F extends proximally along a portion of a respective one of the flex circuit branches 234A-234F. The flexible circuit 222 further includes a plurality of proximal ablation electrodes 244A-244F. As shown, each of the proximal ablation electrodes 244A-244F is located on a respective one of the flex circuit branches 234A-234F.

As further shown, the flexible circuit 222 includes a plurality of spline sensing electrodes 250. In the illustrated embodiment, each of the spline sensing electrodes 250 is disposed within a periphery of one of the proximal ablation electrodes 244A-244F or one of the radial segments 242A-

242F of the distal ablation electrode 238. For example, as shown, each of the distal-most spline sensing electrode 250 is disposed within a periphery of a respective one of the radial segments 242A-242F of the distal ablation electrode 238 and is electrically isolated from the distal ablation electrode 238. Additionally includes a plurality of the more proximally-located spline sensing electrodes 250 is disposed along and within a periphery of a respective one of each of the proximal ablation electrodes 244A-244F and electrically isolated therefrom.

In some embodiments, the structural functionality of the support member 220 can be provided by a suitably designed flexible circuit 222. As such, although the electrode assembly 210 is described in detail as including the support member 220 as a primary structural member, in other embodiments the support member 220 can be omitted in its entirety and the corresponding functionality can be provided by the flexible circuit 222.

In the particular illustrated embodiment, the electroporation catheter 200 includes a central post 258 extending distally from the distal end 209 of the outer shaft 202. As shown, the central post 258 extends partially into the inner space 212, and includes a post electrode 260. As further shown, in the particular illustrated embodiment, an optional irrigation lumen 261 is supported by the central post 258. In embodiments, the central post 258 may house additional components. For example, in embodiments, a magnetic navigation sensor (not shown) may be partially or wholly disposed within the central post 258. However, in other embodiments such a sensor may be located elsewhere on the electroporation catheter 200 (e.g., within the outer shaft 202). In the illustrated embodiment, the electrode assembly 210 further includes a hub sensing electrode 264 centrally located on the flex circuit hub 230.

The post electrode 260 can provide a number of functional advantages. In one example, the post electrode 260 can operate as a reference for unipolar electrograms, in lieu of reliance on surface ECG patch electrodes as are otherwise known in the art. The location of the post electrode 260 for this purpose positions the reference electrode much closer to the tissue being sensed than is possible with the conventional surface ECG approach, which may advantageously minimize far field noise and provide much sharper unipolar electrograms than what are possible using surface ECG electrodes. The post electrode 260 may also be operable to sense and measure other electrical parameters, e.g., voltages between it and the ablation electrodes or other sensing electrodes on the electrode assembly 210, thereby providing data usable for, in some examples, determining the shape of the electrode assembly during use (including when deformed by forces applied by cardiac walls), and displaying shape information via the EAM system 70 (FIG. 1).

In embodiments, the hub sensing electrode 264 allows tissue surface mapping to be conducted in a "forward" manner, eliminating the need to manipulate the electrode assembly 210 to place the spline sensing electrodes 250 against or proximate the tissue to be mapped. The inclusion of the hub sensing electrodes 264 further enhances bipolar sensing capabilities by providing for, in the illustrated embodiment, six additional bi-poles when paired with any of the distal-most spline sensing electrodes 250.

Referring in particular to FIG. 2C, each of the radial segments 242A-242F of the distal ablation electrode 238 includes proximal portion 266A-266F having a proximal end 268A-268F, and a distal portion 270A-270F extending from the distal ablation electrode hub portion 240. As further shown, a radial segment aperture 272 is formed in each proximal portion 266A-266F, and a respective one of the distal-most spline sensing electrodes 250 is disposed within each of the radial segment apertures 272. In the illustrated embodiment, each of the proximal portions 266A-266F has a greater lateral width than that of the corresponding distal portion 270A-270F, at least in part to accommodate the distal-most spline sensing electrodes 250.

Figure 2D:
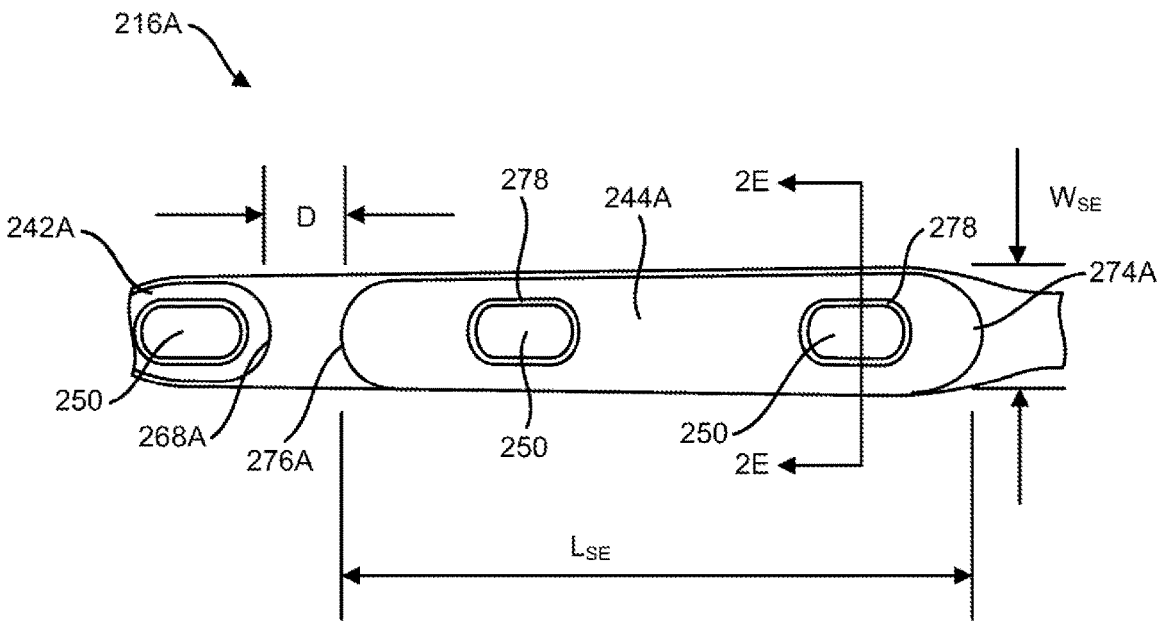
FIG. 2D is an enlarged plan view of a portion of a spline of the electrode assembly shown in FIG. 2B, in accordance with embodiments of the subject matter of the disclosure.

FIG. 2D is an enlarged plan view of a portion of the spline 216A, according to embodiments of the present disclosure. The structural features illustrated in FIG. 2D are representative the splines 216A-216F. As shown, the proximal ablation electrode 244A has a proximal end 274A and a distal end 276A. Additionally, the proximal ablation electrode 244A has a length LSE defined as the distance between the proximal end 274A and the distal end 276A. The proximal ablation electrode 244A further has a width WSE. In embodiments, the width WSE can be substantially constant along the length of the proximal ablation electrode 244A, or alternatively, can vary along the length. In general, the width WSE and the length LSE are dimensioned to provide the desired electrical characteristics for the particular clinical application. In embodiments, the width WSE can range from about 0.25 to 2 millimeters, and the length LSE can range from about 3 to 13 millimeters.

As further shown, the proximal ablation electrode 244A includes a plurality of proximal ablation electrode apertures 278, and wherein one of the spline sensing electrodes 250 is disposed within each of the proximal ablation electrode apertures 278.

Additionally, in the illustrated embodiment, the proximal end 268A of the radial segment 242A of the distal ablation electrode 238 has a semi-circular shape and is spaced by a distance D from the distal end 276A of the proximal ablation electrode 244A, which also has a semi-circular shape. In embodiments, the spacing D can range from about 0.25 to 3 millimeters. In one embodiment, the spacing D is about 0.40 millimeters. In embodiments, the spacing D can be selectively tailored to minimize electrical current from shunting between the distal ablation electrode 238 and the proximal ablation electrodes 244A-244F. The spacing D also can minimize or even eliminate undesirable ablation effects such as localized sparks/arcs or bubble formation. The spacing D also facilitates, in some embodiments, bipolar ablation by configuring the distal ablation electrode 238 and one or more of the proximal ablation electrodes 244A-244F to have opposite polarities (e.g., with one configured as an anode, and the other as a cathode). The semi-circular shapes of the proximal end 268A of the radial segment 242A of the distal ablation electrode 238 and the distal end 276A of the proximal ablation electrode 244A also have unexpected advantages. In particular, this semi-circular profile operates to maximize current distribution along the electrode edges. In general, the radius of the semi-circular shape may be selected to be as large as possible within the constraints imposed by the width WSE of the ablation electrode.

The inventors of the present disclosure have discovered that spacing the proximal end 268A of the distal ablation electrode radial segment 242A from the proximal ablation electrode distal end 276A provides a substantially more effective electric field than that generated by a continuous electrode structure with no such spacing. For example, separating the distal and proximal ablation electrodes allows for selective activation of certain ablation electrodes. Additionally, separating the distal ablation electrode 238 from the proximal ablation electrodes 244A-244F provides for a localized ablation pad of relatively small surface area, which concentrates local current density during ablation and minimizes the amount of energy that may otherwise be shunted away by the blood pool (which as is known, has a relatively low electrical impedance as compared to the target tissue).

Figure 2E:
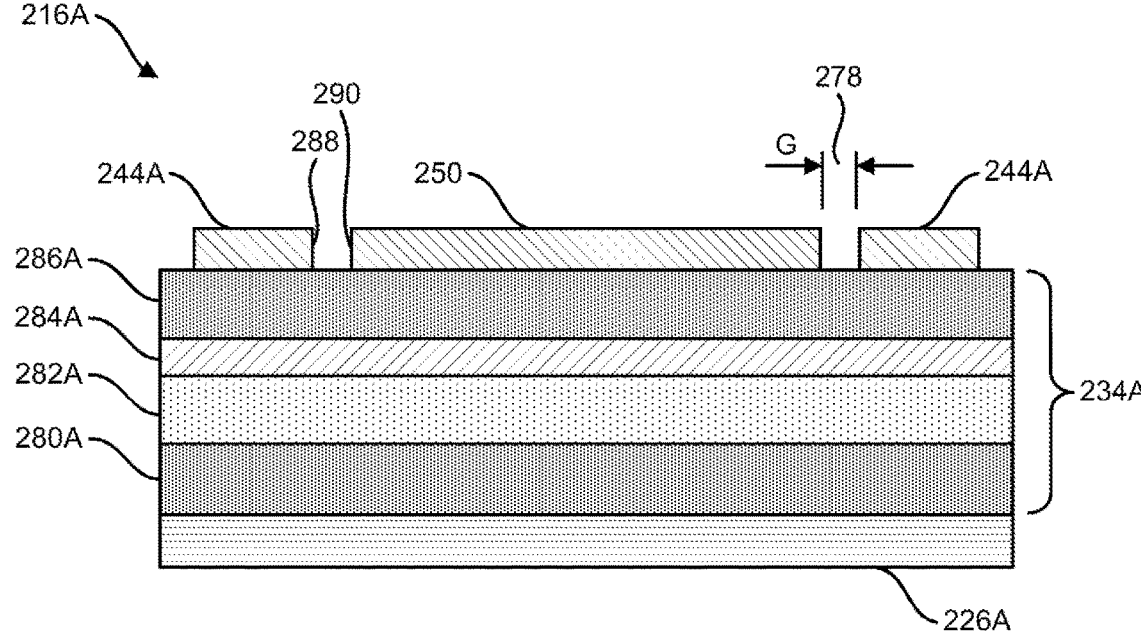
FIG. 2E is a schematic cross-sectional view of a spline of the electrode assembly of FIG. 2B, in accordance with embodiments of the subject matter of the disclosure.

FIG. 2E is a schematic cross-sectional view of the spline 216A taken alone the line 2E-2E in FIG. 2D, illustrating an exemplary configuration of the flex circuit branch 234A. As illustrated in FIG. 2E, the spline 216A includes the support member branch 226A and the flex circuit branch 234A is disposed thereon. As further shown, the flex circuit branch 234A comprises a layered structure that, except as specifically distinguished herein, may be typical of flexible circuits for use in medical device electrode assemblies. In the particular embodiment illustrated in FIG. 2E, the flex circuit branch 234A includes a dielectric base layer 280A disposed over the support member branch 226A, an optional inner flexible adhesive layer 282A over the base layer 280A, a conductive trace layer 284A over the adhesive layer 282A (when present), and a dielectric upper layer 286A over the conductive trace layer 284A. The dielectric materials chosen for the layers 280A and 286A can be any conventional materials suitable for use in flexible circuits for medical devices, e.g., polyamides. It is emphasized that the present disclosure is not limited to the particular flex circuit stacking arrangement illustrated in FIG. 2E, and that the skilled artisan will readily understand alternative arrangements that may be utilized.

As further shown in FIG. 2E, the proximal ablation electrode 244A and the spline sensing electrode 250 are disposed over the upper layer 286A. In embodiments, the electrodes 244A and 250 may have a coating of a suitable biocompatible metal, e.g., gold. In embodiments, the outer surfaces of the electrodes 244A and 250 may be treated to provide the electrical properties desired for the particular clinical application.

As illustrated in FIG. 2E, the proximal ablation electrode aperture 278 is bounded by an inner peripheral surface 288 of the proximal ablation electrode 244A, and an outer peripheral surface 290 of the spline sensing electrode 250 is spaced from the inner peripheral surface 288 of the proximal ablation electrode 244A by a gap G. Conventionally, the skilled artisan would expect to dispose a dielectric material between the outer peripheral surface 290 and the inner peripheral surface 288 of the proximal ablation electrode 244A so as to minimize potential undesirable effects, e.g., bubble formation due to arcing or edge effects at the periphery of the proximal ablation electrode 244A, that may result when the pulsed waveform is delivered to the proximal ablation electrode 244A. However, the inventors of the present disclosure found that by providing the gap G between the outer peripheral surface 290 the spline sensing electrode 250 is spaced from the inner peripheral surface 288 of the proximal ablation electrode 244A, the propensity for bubble formation within the blood pool is substantially reduced as compared to an arrangement where a dielectric material is disposed in this region. These advantageous results can be enhanced by selectively tailoring the dimension of the gap G. In embodiments, the gap G can range from about 0.050 to 0.50 millimeters. In one embodiment, the gap G is about 0.50 millimeters.

Figure 2F:
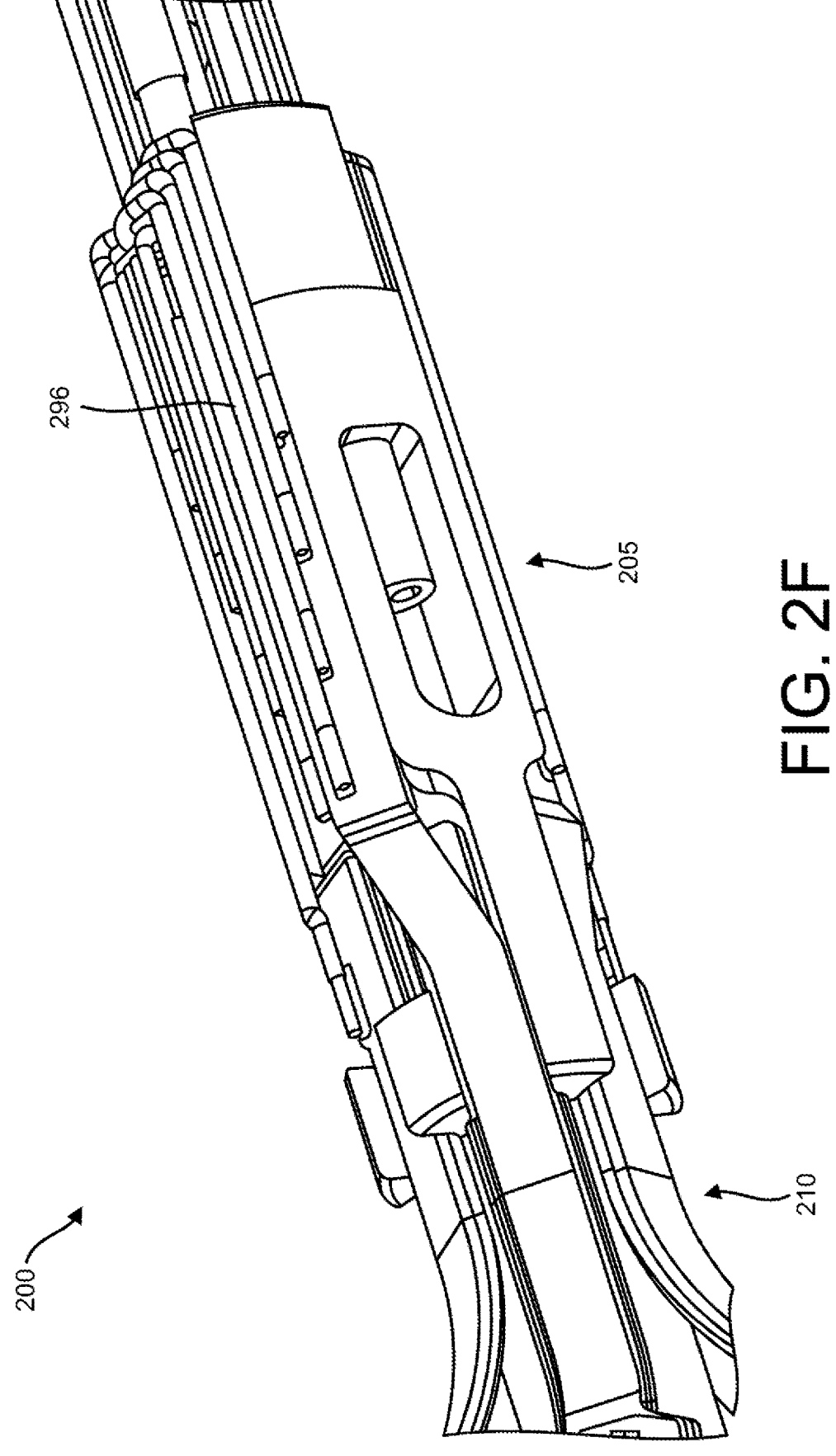
FIGS. 2F-2G are perspective illustrations of portions of the distal portion of the catheter of FIG. 2A, in accordance with embodiments of the subject matter of the disclosure.
Figure 2G:
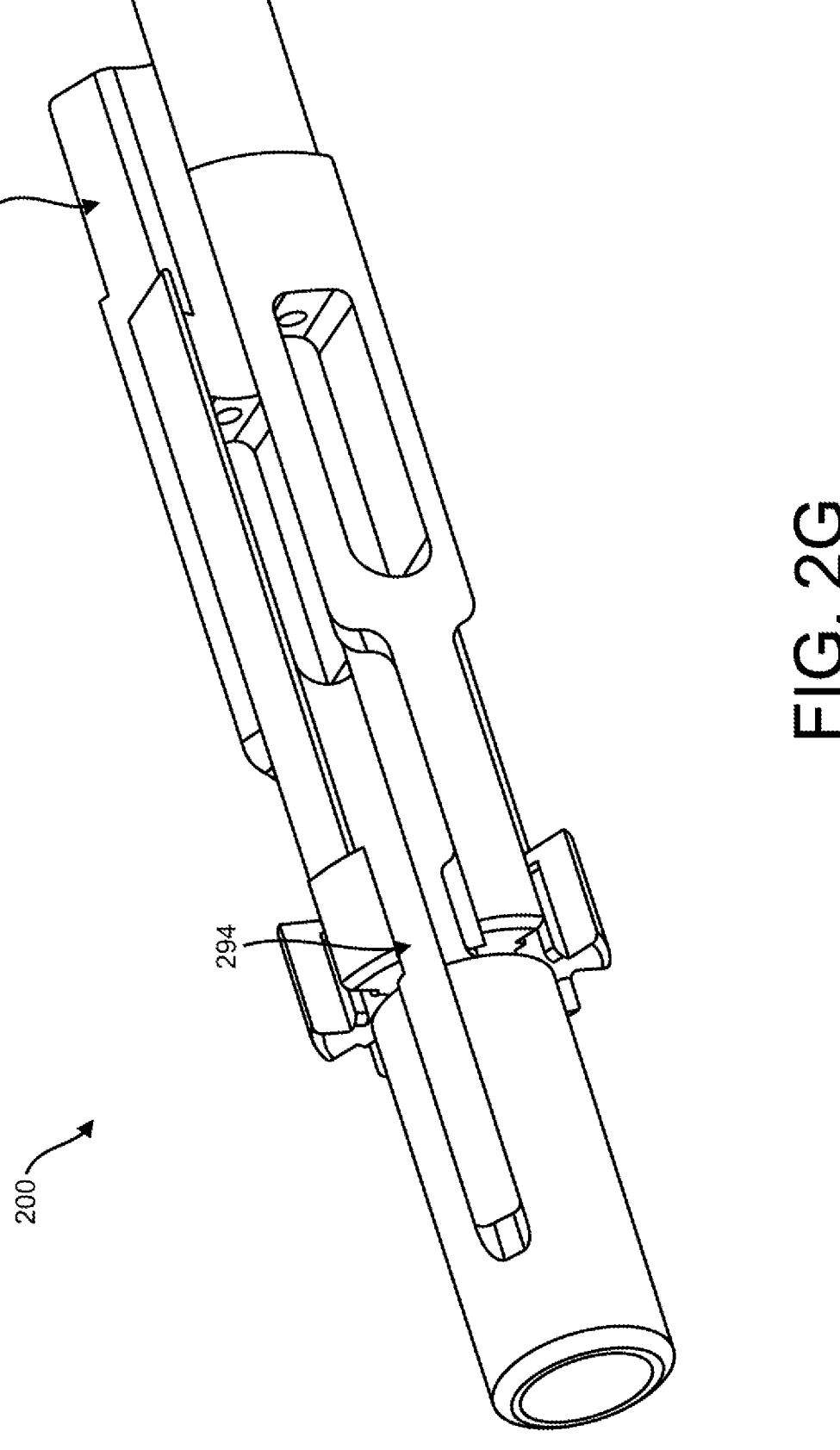

FIGS. 2F-2G are perspective illustrations of portions of the distal portion 205 of the electroporation catheter 200, in accordance with embodiments of the subject matter of the disclosure, illustrating exemplary structural features for connecting the electrode assembly 210 to the shaft 202 (see FIG. 2A). As shown, the electroporation catheter 200 includes a transition component 292 that is secured within the outer shaft 202 (FIG. 2A) and includes various locating features, e.g., slots 294 for locating and connecting the various splines to the shaft 202 and accommodating the connection of electrical conductor wires 296 to the respective flex circuit branches. It is emphasized that the detailed arrangement illustrated in FIGS. 2F and 2G are exemplary only and in no way are intended to limit the scope of the present disclosure.

In the various embodiments, each of the respective proximal ablation electrodes 244A-244F, the distal ablation electrode 238, the spline sensing electrodes 250 and the hub sensing electrode 264 are separately electrically connected to the control system of the electroporation console 130 (FIG. 1) and are individually addressable to provide for a wide range of ablation and sensing modes, e.g., monopolar and bipolar modes. During monopolar ablation operation, an ablation electrode, a group of ablation electrodes, or collectively all of the ablation electrodes on the electrode assembly 210 are electrically coupled in common and configured to operate at one polarity, and an electrode located elsewhere (e.g., a dispersive electrode located on the patient, typically on the back, buttocks, or other suitable anatomical location, or an electrode on a different catheter or probe located outside the cardiac chamber in which the electrode assembly 210 is located) is configured to operate at the opposite polarity. In one example, the distal ablation electrode 238 and all of the proximal ablation electrodes 244A-244F are configured to be electrically in common as an anode or cathode, and an extracorporeal dispersive electrode located on a back patch is configured as the other of the cathode or anode. In other examples, selected proximal ablation electrodes, and optionally the distal ablation electrode 238, can be configured to operate together as an anode or cathode, and the extracorporeal dispersive electrode is configured as the other of the cathode or anode. The preceding example can advantageously allow for selective steering of the resulting electric fields to optimize electroporation effectiveness based on the relative orientation of the ablation assembly 210 and the target tissue. The skilled artisan will readily recognize a wide range of monopolar ablation electrode configurations that may be utilized.

During bipolar ablation operation, a first set of one or more ablation electrodes of the electrode assembly 210 is configured as the anode (or cathode) and a second set of one or more other ablation electrodes of the electrode assembly 210 is configured as the cathode (or anode). In examples, the bipolar ablation electrode sets can comprise electrodes on different splines, or can be formed between one or more of the proximal ablation electrodes and the distal ablation electrode.

In a similar manner, as will be appreciated by the skilled artisan, any of the spline sensing electrodes 250, the post reference electrode 260 or the hub sensing electrode 264 can also be individually addressed for bipolar sensing and mapping an any number of combinations. Additionally, in embodiments, the aforementioned individual addressability allows any of the spline sensing electrodes and/or the hub sensing electrode 264 to be configured by the control system as ablation electrodes to operate in conjunction with the distal ablation electrode 238 and any of the proximal ablation electrodes 244A-244F, in either monopolar or bipolar mode.

Figure 3:
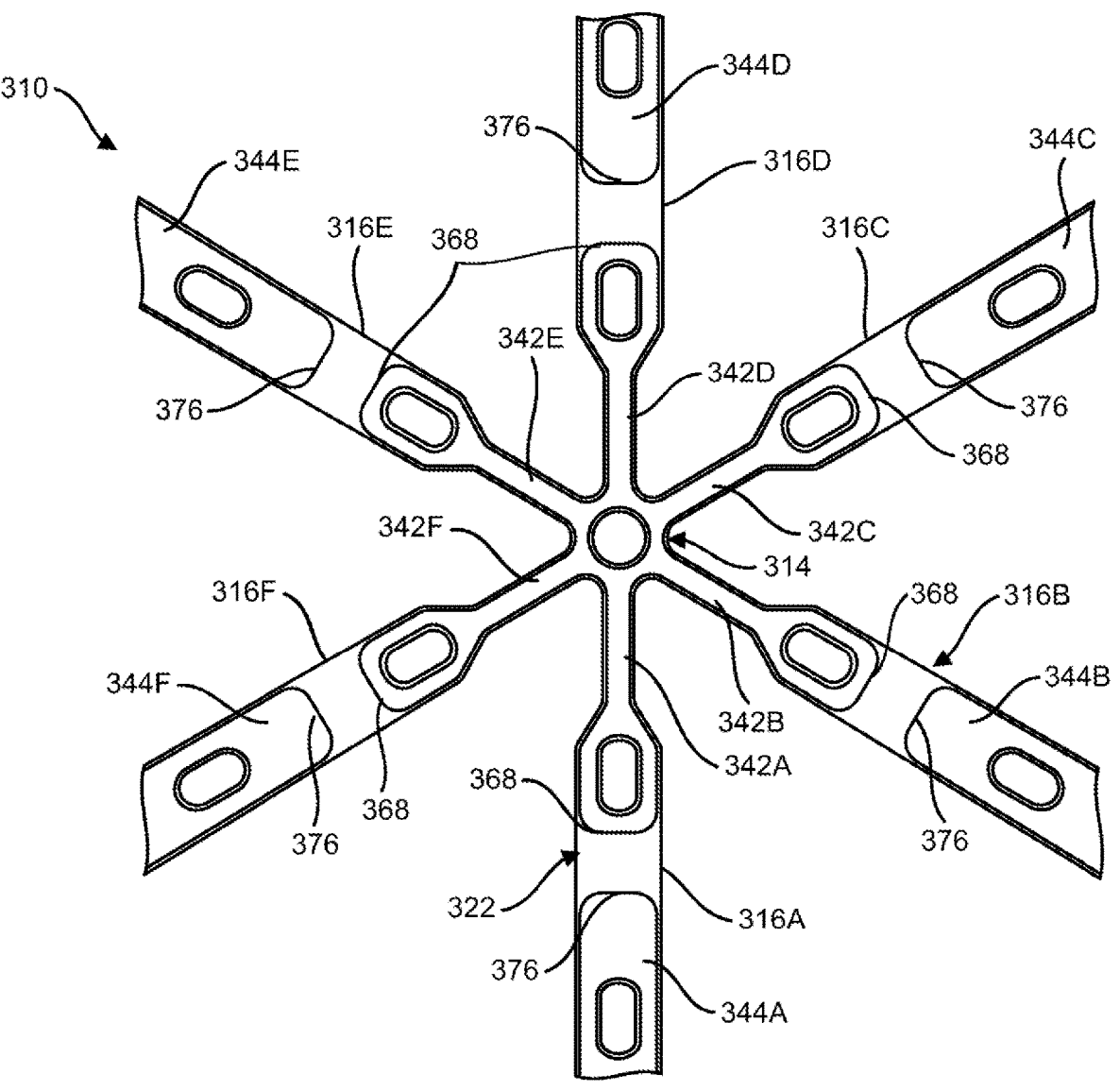
FIGS. 3-6 are plan views alternative electrode assemblies for use in the catheter of FIG. 1, in accordance with embodiments of the subject matter of the disclosure.

FIGS. 3-6 are illustrations of layouts of alternative electrode assemblies for use in the catheter of FIG. 1, in accordance with embodiments of the subject matter of the disclosure. FIG. 3 illustrates a portion of an electrode assembly 310 that is substantially similar to the electrode assembly 210, and includes a central hub portion 314, a plurality of splines 316A-316F and a flex circuit 322. The embodiment of FIG. 3 differs from the electrode assembly 210 in that the proximal ends 368 of each distal ablation electrode radial segment 342F-342F is generally linear (i.e., is not semi-circular), and the distal end 376 of each of the proximal ablation electrodes 344A-344F is also generally linear, such that the opposing surfaces of the proximal end 368 of each radial segment 342A-342F and the opposing distal end of the corresponding proximal ablation electrode 344A-344F are generally parallel to one another.

Figure 4:
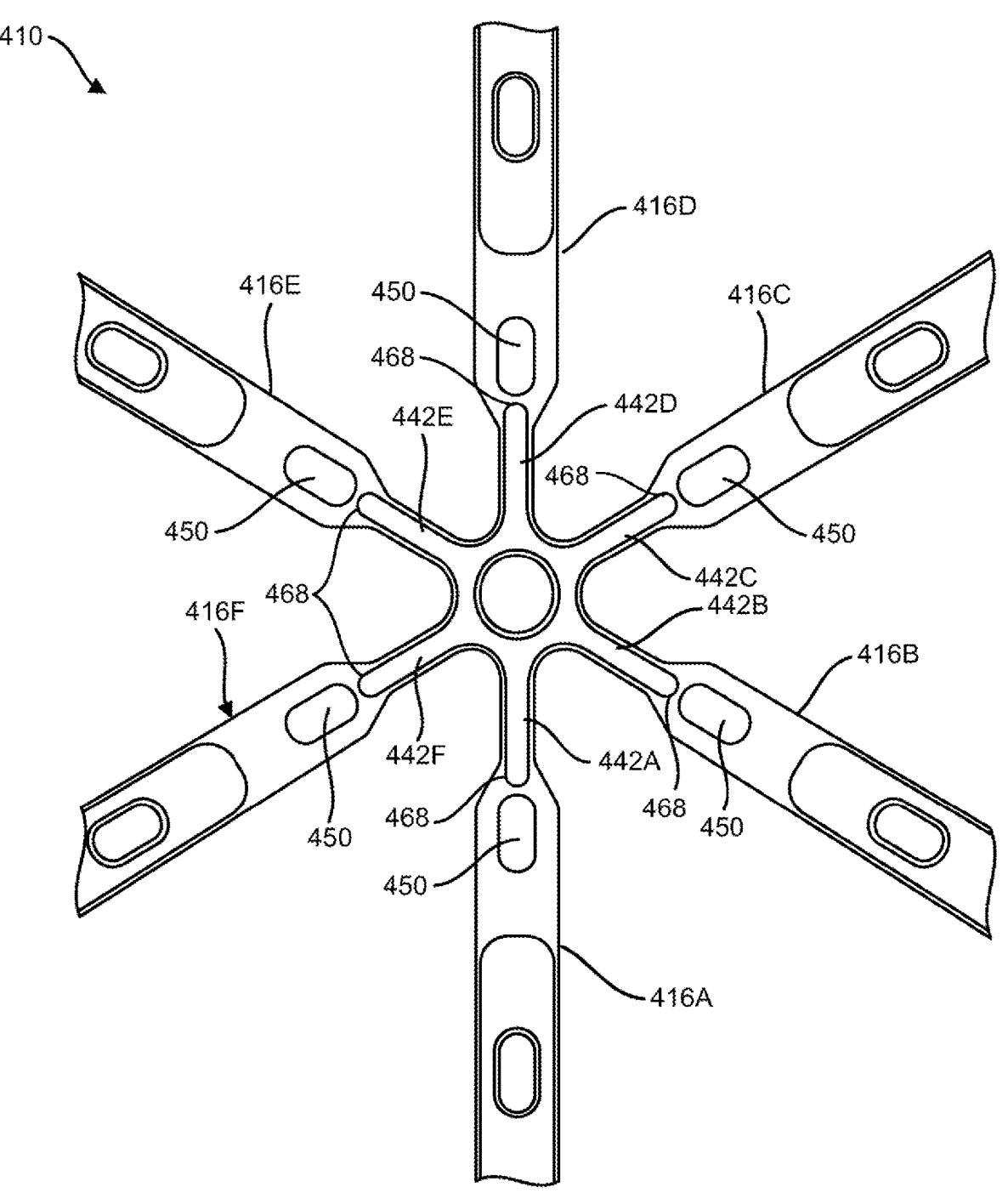

FIG. 4 illustrates a portion of an electrode assembly 410 that includes a central hub portion 414, a plurality of splines 416A-416F and a flex circuit 422. As will be appreciated, the electrode assembly 410 also includes a support member (not shown) having substantially the same configuration of the support member 220 of the electrode assembly 210. The embodiment of FIG. 4 differs from the electrode assembly 210 in that the proximal end 468 of each distal ablation electrode radial segment 442A-442F terminates distally of and is spaced from the distal-most spline sensing electrode 450 on each spline.

Figure 5:
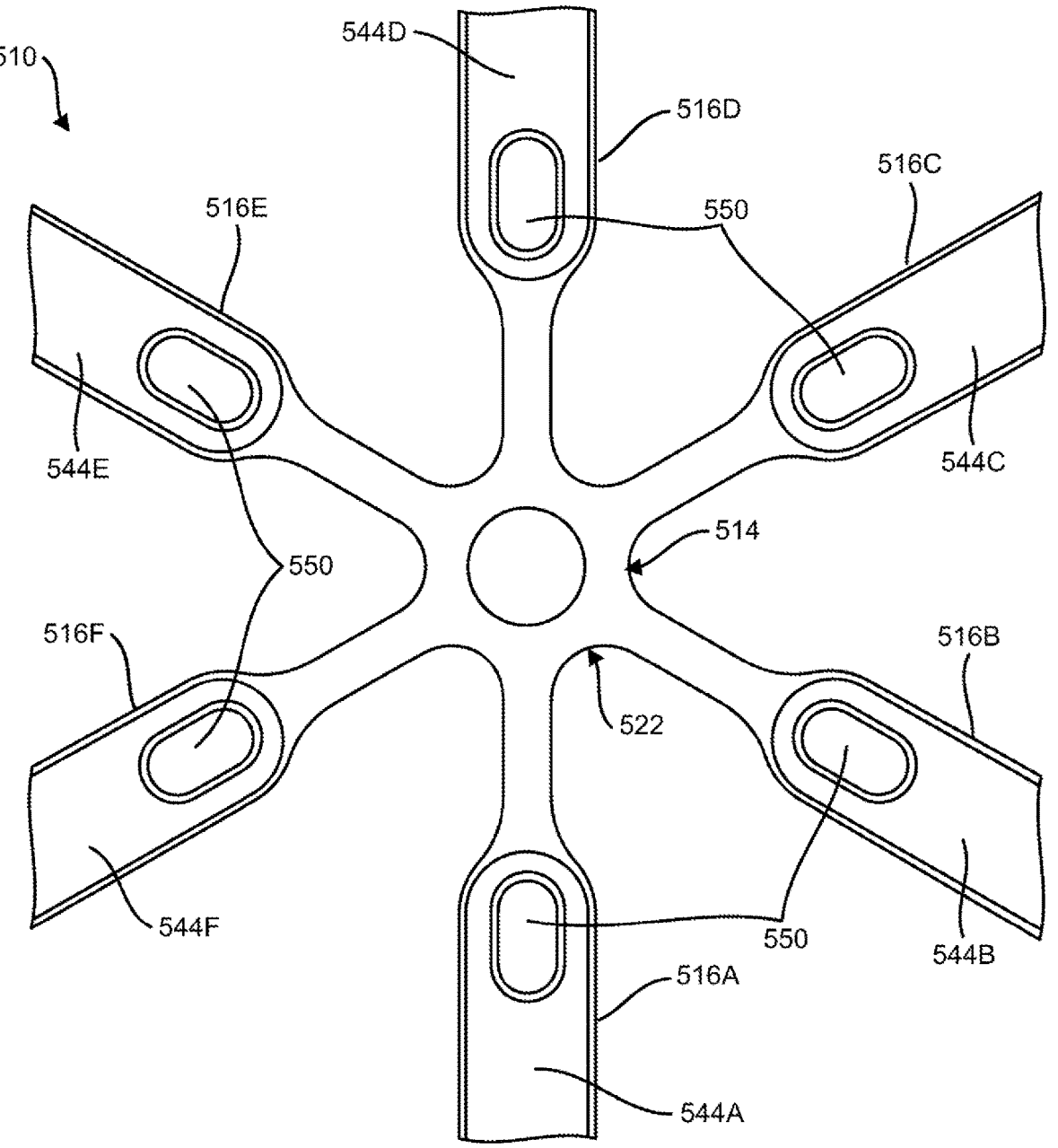

FIG. 5 illustrates a portion of an electrode assembly 510 that includes a central hub portion 514, a plurality of splines 516A-516F and a flex circuit 522. As will be appreciated, the electrode assembly 510 also includes a support member (not shown) having substantially the same configuration of the support member 220 of the electrode assembly 210. The flex circuit 522 differs from those described previously in that it does not include a distal ablation electrode, and distal-most spline sensing electrode 548 on each spline is located within the periphery of the respective proximal ablation electrode 544A-544F.

Figure 6:
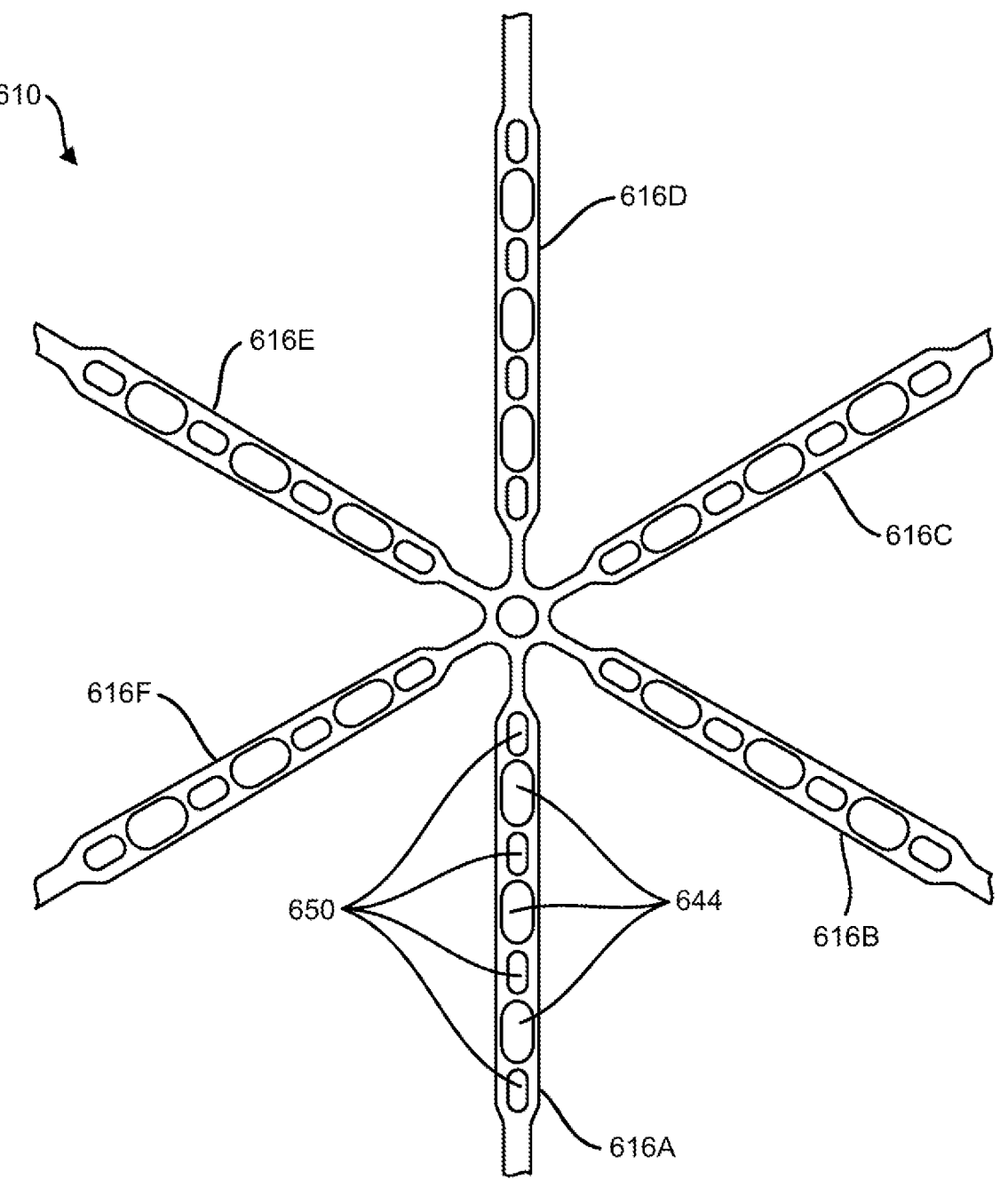

FIG. 6 illustrates a portion of an electrode assembly 610 that includes a central hub portion 614, a plurality of splines 616A-616F and a flex circuit 622. As further shown, the flex circuit 622 includes a flex circuit hub 630 and a plurality of flex circuit branches 634A-634F. As will be appreciated, the electrode assembly 610 also includes a support member (not shown) having substantially the same configuration of the support member 620 of the electrode assembly 610.

As further shown, the flex circuit 622 further includes, on each of the splines 616A-616F, a series of alternating proximal ablation electrodes 644 and spline sensing electrodes 650 spaced from one another, i.e., none of the spline sensing electrodes 650 are disposed within the periphery of any of any of the proximal ablation electrodes 644. Additionally, in the illustrated embodiment the flex circuit 622 does not include a distal ablation electrode, although in other embodiments a distal ablation electrode may be included.

As discussed with the electrode assembly 210, in the electrode assemblies 310, 410, 510 and 610, all of the illustrated ablation and sensing electrodes are individually addressable by the control system, thus providing for a wide range of monopolar or bipolar ablation and unipolar or bipolar sensing capabilities. Similarly, any or all of the various sensing electrodes can be configured to operate as ablation electrodes when desired for a given clinical procedure.

In the embodiments described and illustrated herein, each of the ablation assemblies has six splines. It is emphasized, however, that this is for illustration purposes, and thus the skilled artisan will readily recognize that for a given clinical application more or fewer than six splines may be included.

FIGS. 7A-7D are schematic cross-sectional views of alternative spline configurations that may be utilized for any of the catheter electrode assemblies described herein in accordance with the various embodiments. In general, the embodiments of FIGS. 7A-7D are configured to be substantially atraumatic, e.g., lacking relatively sharp edges.

Figure 7A:
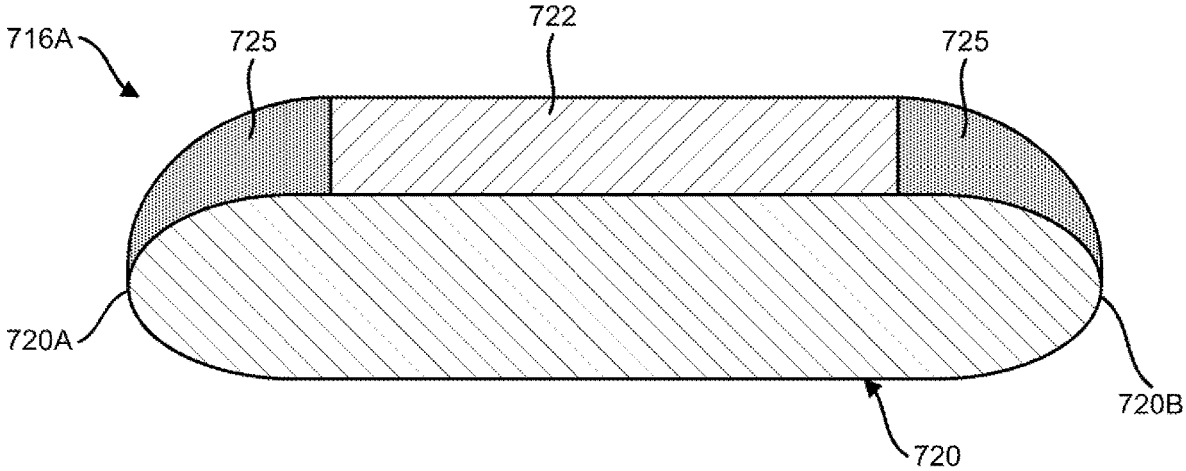
FIGS. 7A-7D are schematic cross-sectional views of alternative spline configurations for the catheter of FIG. 1, in accordance with embodiments of the subject matter of the disclosure.

FIG. 7A illustrates a spline 716A the catheter of FIG. 1, in accordance with embodiments of the subject matter of the disclosure. As shown, the spline 716A includes a support member 720 and a flexible circuit 722 disposed over and secured to the support member 720. As will be appreciated, the support member 720 may correspond to the support member 220 described in connection with the embodiments of FIGS. 2A-2G. As shown, the support member 720 has a substantially obround cross-sectional shape, such that it has opposite lateral sides 720A, 720B that are substantially rounded or semi-circular in shape. In embodiments, the lateral sides 720A, 720B may be formed by any number of manufacturing techniques known in the art, e.g., by machining or etching a flat section of material.

The spline 716A includes a flexible polymer layer 725, which may be an adhesive material, extending laterally from lateral sides of the flex circuit 722. As shown, the flexible polymer layer 725 has a contoured outer surface that provides a substantially smooth transition with the lateral sides 720A, 720B of the support member 720. This smooth transition can have mechanical, clinical and electrical benefits. For example, the illustrated configuration eliminates relatively sharp edges on the spline, which if present could have adverse effects on tissue (e.g., myocardial tissue) contacting the spline 716A. Additionally, the polymer layer 725 can reduce or minimize edge effects that could otherwise be present at the various ablation electrodes on the flex circuit 722. In embodiments, the polymer layer 725 may comprise a flexible adhesive material that operates to attach the flex circuit 722 to the support member 720.

Figure 7B:
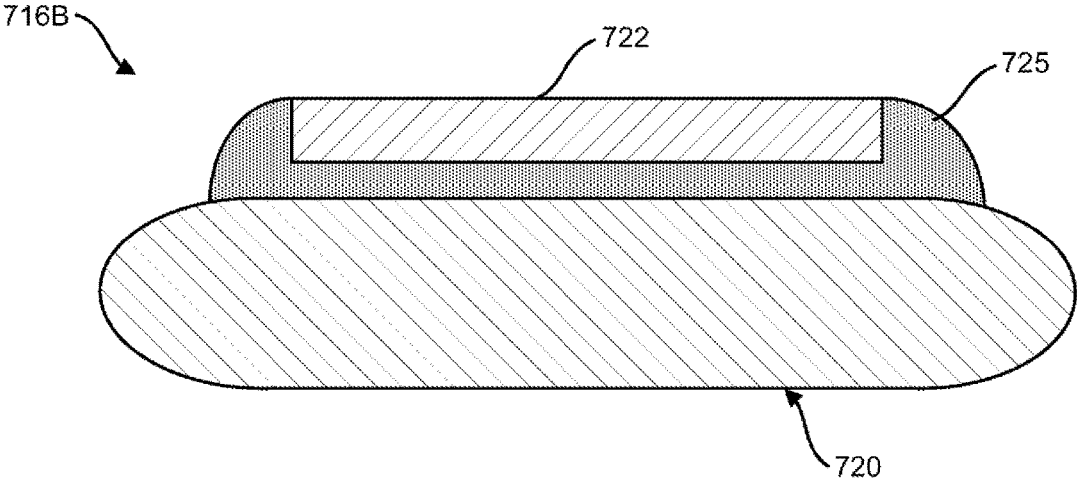

FIG. 7B illustrates an alternative spline 716B that is in respects similar to the spline 716A, and includes a support member 720, a flex circuit 722 and a flexible polymer layer 725 that forms a contoured outer surface providing an atraumatic transition between the lateral ends of the flex circuit 722 and the support member 720. As shown, in the embodiment of FIG. 7B, a portion of the flexible polymer layer 725 is disposed between the support member 720 and the flexible circuit 722. In this embodiment, this portion of the flexible polymer layer 725 can, in addition to operating to secure the flexible circuit 722 to the support member 720, provide a stress-relief function to compensate for differing mechanical properties (e.g., flexural moduli, stiffness, and the like) of the support member 720 and the flexible circuit 722.

Figure 7C:
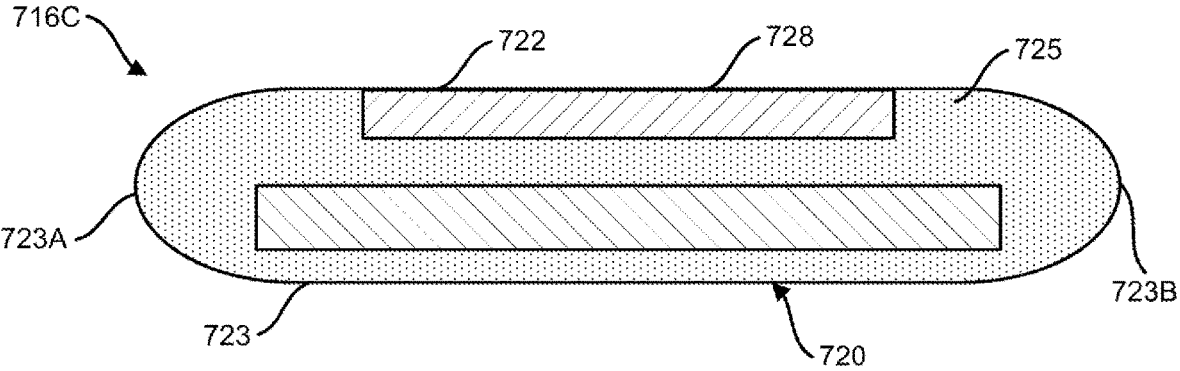

FIG. 7C illustrates an alternative configuration of a spline 716C that includes a support member 720 and a flexible circuit 722, and an outer member 723 having an obround shape with rounded or semi-circular opposite ends 723A, 722B. As shown, the support member 720 is entirely disposed within the outer member 723, and the flexible circuit 722 is substantially so disposed other than an outer surface 728 containing the various electrodes described above in connection with the various other embodiments. Additionally, the interior of the outer member 723 is filled with a flexible polymer or adhesive material 725 that encapsulates the support member 720 and the portions of the flexible circuit 722 disposed within the outer member 723.

Figure 7D:
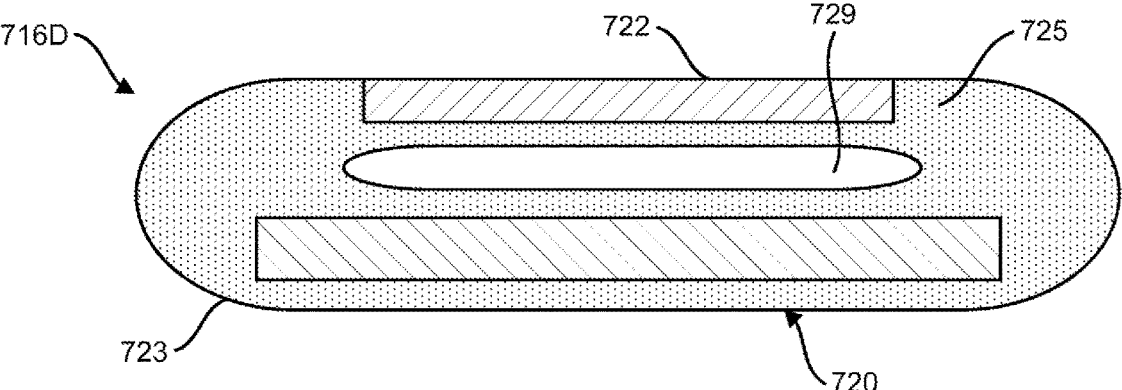

FIG. 7D illustrates yet another alternative configuration of a spline 716D that is substantially similar to the spline 716C, but further includes an inner air gap 729 formed within the polymer material 725 between the support member 720 and the flexible circuit 722. In embodiments, the air gap 729 can provide a mechanical interface between the support member 720 and the flexible circuit 722 to compensate for the different structural properties of these components. In embodiments, the air gap 729 may be formed by placing a mandrel between the support member 720 and the flexible circuit 722 which is removed after the polymer material 725 is deposited into the outer member 723. Alternatively, the air gap 729 may be provided via an additional tubular member that remains in place following deposition of the polymer material.

It is well understood that methods that include one or more steps, the order listed is not a limitation of the claim unless there are explicit or implicit statements to the contrary in the specification or claim itself. It is also well settled that the illustrated methods are just some examples of many examples disclosed, and certain steps may be added or omitted without departing from the scope of this disclosure. Such steps may include incorporating devices, systems, or methods or components thereof as well as what is well understood, routine, and conventional in the art.

The connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements. The scope is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art with the benefit of the present disclosure to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A catheter for ablating cardiac tissue through irreversible electroporation, the catheter comprising:

a tubular outer shaft having a proximal end and an opposite distal end;

an electrode assembly extending distally from the distal end of the outer shaft, the electrode assembly defining a distally located central hub portion and a plurality of splines each including a distal end portion extending from the central hub portion, and a proximal end portion attached to and constrained by the outer shaft, the electrode assembly comprising:

a support member having a support member hub and a plurality of support member branches extending proximally from the support member hub;

a flexible circuit attached to an outer surface of the support member and having a flex circuit hub disposed over the support member hub, and a plurality of flex circuit branches, each of the flex circuit branches disposed over a respective one of the support member branches, the flexible circuit further including:

a distal ablation electrode including an ablation electrode hub portion located on the flex circuit hub, and a plurality of radial segments integrally formed with the ablation electrode hub portion, each of the radial segments extending proximally along a portion of a respective one of the flex circuit branches and terminating in a proximal end; and a plurality of proximal ablation electrodes, each of the proximal ablation electrodes located on a respective one of the flex circuit branches and having a distal end spaced from the proximal end of the adjacent radial segment of the distal ablation electrode.

2. The catheter of claim 1, wherein the flexible circuit further comprises a plurality of spline sensing electrodes located on each spline, wherein a distal-most spline sensing electrode on each spline is disposed within a periphery of each of the radial segments of the distal ablation electrode and is electrically isolated from the distal ablation electrode, and wherein one or more of the plurality of spline sensing electrodes is disposed within a periphery of each of the proximal ablation electrodes and is electrically isolated therefrom.

3. The catheter of claim 2, wherein the proximal end of each radial segment has a semi-circular shape.

4. The catheter of claim 3, wherein the distal end of each proximal ablation electrode has a semi-circular shape.

5. The catheter of claim 2, wherein each of the proximal ablation electrodes includes one or more proximal ablation electrode apertures formed therein, and wherein one of the spline sensing electrodes is disposed within a respective one of the proximal ablation electrode apertures.

6. The catheter of claim 5, wherein each proximal ablation electrode aperture is bounded by respective inner peripheral surface of the proximal ablation electrode, and wherein an outer peripheral surface of each spline sensing electrode is spaced from the respective inner peripheral surface of the proximal ablation electrode.

7. The catheter of claim 2, wherein each of the radial segments of the distal ablation electrode includes a proximal portion having a radial segment aperture formed therein, and wherein each of the distal-most spline sensing electrodes is disposed within a respective one of the radial segment apertures.

8. The catheter of claim 7, wherein each radial segment aperture is bounded by respective inner peripheral surface of the radial segment, and wherein an outer peripheral surface of each distal-most spline sensing electrode is spaced from the respective inner peripheral surface of the radial segment.

9. The catheter of claim 2, further comprising a hub sensing electrode centrally located on the central hub portion of the electrode assembly.

10. The catheter of claim 2, further comprising a central post extending distally from the distal end of the tubular shaft and into an inner space defined by the electrode assembly when the electrode assembly is in an expanded configuration, the central post including a reference electrode.

11. A catheter for ablating cardiac tissue through irreversible electroporation, the catheter comprising:

a tubular outer shaft having a proximal end and an opposite distal end;

an electrode assembly extending distally from the distal end of the outer shaft, the electrode assembly defining a distally-located central hub portion and a plurality of splines each including a distal end portion extending proximally from the central hub portion, and a proximal end portion attached to and constrained by the outer shaft, the electrode assembly comprising:

a support member formed from a superelastic material and having a support member hub and a plurality of support member branches integrally formed with and extending proximally from the support member hub;

a flexible circuit attached to an outer surface of the support member and having a flex circuit hub disposed over the support member hub, and a plurality of flex circuit branches integrally formed with the flex circuit hub, each of the flex circuit branches disposed over a respective one of the support member branches, the flexible circuit further including:

a distal ablation electrode including an ablation electrode hub portion located on the flex circuit hub, and a plurality of radial segments integrally formed with the ablation electrode hub portion, each of the radial segments extending proximally along a portion of a respective one of the flex circuit branches;

a plurality of proximal ablation electrodes, each of the proximal ablation electrodes located on a respective one of the flex circuit branches;

a plurality of spline sensing electrodes, including a plurality of distal spline sensing electrodes each being disposed within a periphery of a respective one of the radial segments of the distal ablation electrode and electrically isolated from the distal ablation electrode, and one or more proximal spline sensing electrodes disposed within a periphery of each of the proximal ablation electrodes and electrically isolated therefrom.

12. The catheter of claim 11, wherein each of the proximal ablation electrodes has a proximal end and a distal end having a semi-circular shape, and wherein each of the radial segments has a proximal end having a semi-circular shape.

13. The catheter of claim 11, wherein each of the proximal ablation electrodes includes one or more proximal ablation electrode apertures formed therein, and wherein each of the proximal spline sensing electrodes is disposed within a respective one of the proximal ablation electrode apertures.

14. The catheter of claim 13, wherein each proximal ablation electrode aperture is bounded by respective inner peripheral surface of the proximal ablation electrode, and wherein an outer peripheral surface of each proximal spline sensing electrode is spaced from the respective inner peripheral surface of the proximal ablation electrode.

15. The catheter of claim 11, wherein each of the radial segments of the distal ablation electrode includes proximal portion having a radial segment aperture formed therein, and wherein each of the distal spline sensing electrodes is disposed within a respective one of the radial segment apertures.

16. The catheter of claim 15, wherein each radial segment aperture is bounded by respective inner peripheral surface of the radial segment, and wherein an outer peripheral surface of each distal spline sensing electrode is spaced from the respective inner peripheral surface of the radial segment.

17. A catheter for ablating cardiac tissue through irreversible electroporation, the catheter comprising:

a tubular outer shaft having a proximal end and an opposite distal end;

an electrode assembly extending distally from the distal end of the outer shaft, the electrode assembly comprising a flexible circuit having a distally located central flex circuit hub and a plurality of flex circuit branches extending proximally from the hub portion, each of the flex circuit branches defining, at least in part, an electrode assembly spline and including a proximal end portion attached to and constrained by the outer shaft, the flexible circuit further including:

a distal ablation electrode including an ablation electrode hub portion located on the flex circuit hub, and a plurality of radial segments integrally formed with the ablation electrode hub portion, each of the radial segments extending proximally along a portion of a respective one of the flex circuit branches and terminating in a proximal end; and a plurality of proximal ablation electrodes, each of the proximal ablation electrodes located on a respective one of the flex circuit branches and having a distal end spaced from the proximal end of the adjacent radial segment of the distal ablation electrode.

18. The catheter of claim 17, wherein the proximal end of each radial segment has a semi-circular shape, and wherein the distal end of each proximal ablation electrode has a semi-circular shape.

19. The catheter of claim 18, wherein the flexible circuit further comprises a plurality of spline sensing electrodes located on each spline, wherein a distal-most spline sensing electrode on each spline is disposed within a periphery of each of the radial segments of the distal ablation electrode and is electrically isolated from the distal ablation electrode, and wherein one or more of the plurality of spline sensing electrodes is disposed within a periphery of each of the proximal ablation electrodes and electrically isolated therefrom.

20. The catheter of claim 19, wherein the flexible circuit further comprises a hub sensing electrode centrally located on the flex circuit hub.

* * * * *